(12) United States Patent
Ogasawara et al.

(10) Patent No.: US 10,059,932 B2
(45) Date of Patent: Aug. 28, 2018

(54) MUTANT OF CELLULASE-PRODUCING MICROORGANISM, PRODUCTION METHOD OF CELLULASE AND PRODUCTION METHOD OF CELLO-OLIGOSACCHARIDE

(71) Applicants: NAGAOKA UNIVERSITY OF TECHNOLOGY, Niigata (JP); INPEX CORPORATION, Tokyo (JP)

(72) Inventors: Wataru Ogasawara, Niigata (JP); Takashi Yamaguchi, Niigata (JP); Yosuke Shida, Niigata (JP); Yoshiro Ishii, Tokyo (JP); Tatsuki Wakayama, Tokyo (JP); Yoshiro Konda, Tokyo (JP)

(73) Assignees: NAGAOKA UNIVERSITY OF TECHNOLOGY, Niigata (JP); INPEX CORPORATION, Tokyo (JP)

( * ) Notice: Subject to any disclaimer, the term of this patent is extended or adjusted under 35 U.S.C. 154(b) by 0 days.

(21) Appl. No.: 14/776,679

(22) PCT Filed: Mar. 14, 2014

(86) PCT No.: PCT/JP2014/056982
§ 371 (c)(1),
(2) Date: Sep. 14, 2015

(87) PCT Pub. No.: WO2014/142325
PCT Pub. Date: Sep. 18, 2014

(65) Prior Publication Data
US 2016/0046918 A1 Feb. 18, 2016

(30) Foreign Application Priority Data
Mar. 15, 2013 (JP) .................................. 2013-053166

(51) Int. Cl.
*C12N 1/21* (2006.01)
*C12N 9/42* (2006.01)
*C12P 19/14* (2006.01)
*C12P 19/04* (2006.01)
*C12N 15/80* (2006.01)

(52) U.S. Cl.
CPC ........... *C12N 9/2437* (2013.01); *C12N 9/244* (2013.01); *C12N 9/2434* (2013.01); *C12N 9/2445* (2013.01); *C12N 15/80* (2013.01); *C12P 19/04* (2013.01); *C12P 19/14* (2013.01); *C12Y 302/01004* (2013.01)

(58) Field of Classification Search
None
See application file for complete search history.

(56) References Cited

U.S. PATENT DOCUMENTS

| | | | | |
|---|---|---|---|---|
| 5,328,841 A | * | 7/1994 | Lorch | ............... C11D 3/38645 435/209 |
| 5,650,322 A | * | 7/1997 | Clarkson | ............ C11D 3/38645 435/209 |
| 5,997,913 A | * | 12/1999 | Fowler | .................... C12G 1/00 426/15 |

FOREIGN PATENT DOCUMENTS

| | | | |
|---|---|---|---|
| JP | 04-075594 | 3/1992 | |
| JP | 05-115293 | 5/1993 | |
| JP | 08-033496 | 2/1996 | |
| JP | 2006-034206 | 2/2006 | |
| JP | 2006-204294 | 8/2006 | |
| WO | WO 2005/001036 A2 * | 1/2005 | |
| WO | WO 2012125951 A1 * | 9/2012 | ........... C12N 9/2445 |
| WO | 2013028927 | 2/2013 | |

OTHER PUBLICATIONS

Santos et al., Curr. Opin. Chem. Biol. 12:168-176, 2008.*
Lehmann et al., Biotechnol. Bioengineer. 113:1001-1010, 2015.*
UniProt Database Accession No. P07981, Mar., 2013, 3 pages.*
Hartl et al., "Sequential gene deletions in Hypocrea jecorina using a single blaster cassette", Curr. Genet. 48:204-211, 2005.*
Portnoy et al., "Differential Regulation of the Cellulase Transcription Factors XYR1, ACE2, and ACE1 in Trichoderma reesei Strains Producing High and Low Levels of Cellulase", Eukaryotic Cell, 10:262-271, 2011.*
Liu et al., World J. Microbiol. Biotechnol. 22:1301-1305, 2006 (Year: 2006).*
Bhat et al., Biotechnol. Adv. 15:583-620, 1997 (Year: 1997).*
Lindner et al., "Purification and properties of a carboxymethylcellulase from Sclerotium rolfsii", Biochim. Biophys. Acta 746:160-167, 1983, abstract only (Year: 1983).*
Extended European Search Report for European Application No. 14764708.5 dated Jul. 12, 2016, 6 pgs.
International Search Report for PCT/JP2014/056982 dated Jun. 17, 2014, 6 pgs.
M. Komatsu, et al., Biomass Bunkai ni Hitsuyo na Trichoderma reesei Toka Koso no Senbatsu, Japan Society for Bioscience, Biotechnology, and Agrochemistry Taikai Koen Yoshishu, vol. 2013, Mar. 5, 2013, 2C12p18.
M. Komatsu, et al., Trichoderma reesei Yurai Toka Koso no Biomass Bunkai ni Okeru Yakuwari, Japan Society for Bioscience, Biotechnology, and Agrochemistry Taikai Koen Yoshishu, vol. 2012, Mar. 5, 2012, 3B03a04.

(Continued)

*Primary Examiner* — David J Steadman
(74) *Attorney, Agent, or Firm* — Procopio, Cory, Hargreaves & Savitch LLP

(57) ABSTRACT

An object is to provide a mutant of a cellulase-producing microorganism which produces a cellulase capable of preferentially producing a cello-oligosaccharide during the selective production of the cello-oligosaccharide through enzymolysis of a cellulosic material in the presence of the cellulase, a method for producing the cellulase and a method for producing a cello-oligosaccharide using the cellulase. The present invention relates to a mutant of a cellulase-producing microorganism, in which cellobiohydrolase and β-glucosidase genes are disrupted.

3 Claims, 19 Drawing Sheets

Specification includes a Sequence Listing.

(56) References Cited

OTHER PUBLICATIONS

Y. Saito, et al., Trichoderma reesei Endoglucanase I Oyobi II no Biomass Bunkai ni Okeru Yakuwari, Japan Society for Bioscience, Biotechnology, and Agrochemistry Taikai Koen Yoshishu, vol. 2012, Mar. 5, 2012, 3B03a04.
Cellulase, issue from Kodansha Scientific, 1987, pp. 97-104.

* cited by examiner

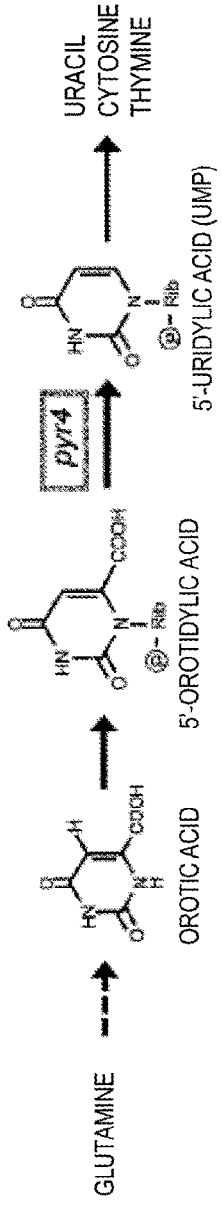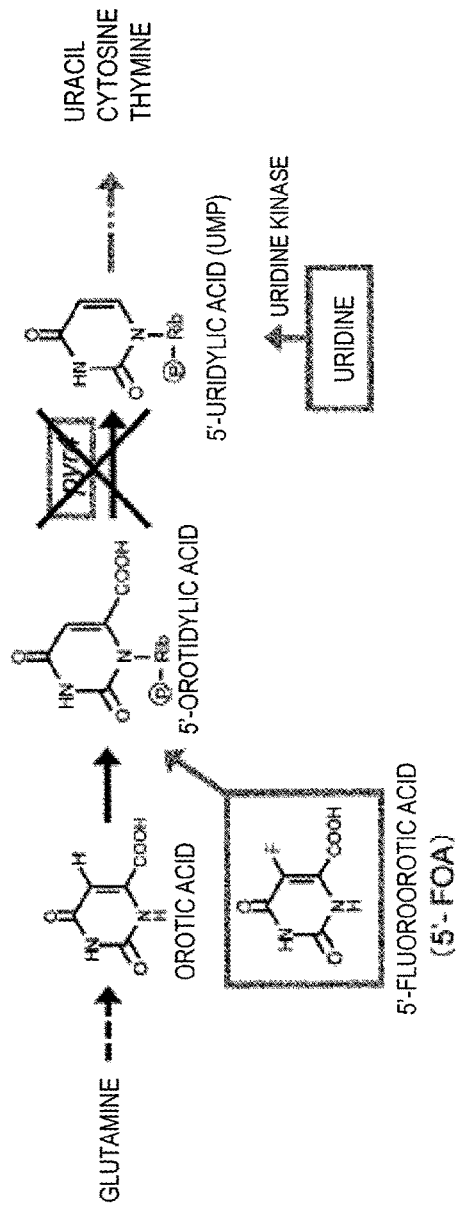
Fig. 6

MUTANT OF CELLULASE-PRODUCING MICROORGANISM, PRODUCTION METHOD OF CELLULASE AND PRODUCTION METHOD OF CELLO-OLIGOSACCHARIDE

TECHNICAL FIELD

The present invention relates to a mutant of a cellulase-producing microorganism, a production method thereof, a method for producing a cellulase using the mutant and a method for producing a cello-oligosaccharide using the cellulase.

BACKGROUND ART

A cello-oligosaccharide is an oligosaccharide formed by polymerization of two to six glucose molecules and is a linear oligosaccharide in which two to six glucopyranose units are linked by β-1,4-glycosidic bonds. It is anticipated that cello-oligosaccharides will serve as materials that can be used in the fields of functional foods, energy, feed, chemical engineering products or the like.

In a known method for producing cello-oligosaccharides, decomposition of cellulose as a starting material by cellulases is utilized. As shown in FIG. 1, the mechanism of decomposition of cellulose by cellulases includes (1) reaction where cello-oligosaccharides including cellobiose are produced from cellulose by the effect of cellulose degrading enzymes, (2) reaction where glucose is produced from cellulose and (3) reaction where glucose is produced from cello-oligosaccharides by the effect of a β-glucosidase (NPL 1).

As shown in FIG. 1, there are three types of enzymatic activity for cellulases: endoglucanases which randomly decompose cellulose (sometimes abbreviated to EG below); cellobiohydrolases which release cellobiose from the ends of cellulose chains (sometimes abbreviated to CBH below); and β-glucosidases which decompose cellobiose into two glucose molecules (sometimes abbreviated to BGL below).

In order to increase the productivity of cello-oligosaccharides, it is effective to inhibit the decomposition of cello-oligosaccharides by inhibiting a β-glucosidase contained in cellulases and inhibiting the decomposition of the cello-oligosaccharides into glucose. With respect to methods for inhibiting a β-glucosidase contained in cellulases, various attempts including enzyme fractionation using fractionation by chromatography shown in FIG. 2 have been made.

PTL 1 discloses a method for selectively producing cellobiose from cellulose using cellulases obtained by adsorbing cellulases onto a weak-acid cation exchange resin which has been equilibrated at pH 3.5 to 5.0 to remove a β-glucosidase from the cellulases.

PTL 2 discloses a method for producing cello-oligosaccharides by adsorbing the enzyme components contained in cellulases, except for β-glucosidases, onto cellulose or a cellulose-containing substance in advance and then conducting enzymolysis.

PTL 3 describes a method for separating and removing a β-glucosidase from cellulases characterized by filling a tube or tower reactor with a cellulosic material, letting a cellulase solution that contains a cellobiohydrolase and contains, as impurities, a β-glucosidase continuously pass through the reactor in one direction and thus selectively separating and removing the fraction containing the β-glucosidase.

These conventional methods can reduce the amount of β-glucosidase that contaminates during the production step of cellobiose, and cellobiose can be obtained selectively. However, these methods require a step of adsorbing cellulases onto a solid fraction and a step of separating the solid fraction and thus have problems because the process is complex and costs are high.

In addition, a method for inhibiting the β-glucosidase activity has been developed, and PTL 4 describes a method for producing cellobiose in which δ-gluconolactone or gluconic acid, which is a β-glucosidase inhibitor, is made exist during the decomposition of cellulose by cellulases.

In the method described in PTL 5, glucose oxidase is made exist during the decomposition of cellulose by cellulases and δ-gluconolactone is produced from the produced glucose, and as a result it is attempted to inhibit the β-glucosidase activity.

However, the practical application of these methods has been difficult because of the complexity of the separation of cellobiose as the product from δ-gluconolactone, high price of δ-gluconolactone and the like.

CITATION LIST

Patent Literature

PTL 1: JP-A-5-115293
PTL 2: JP-A-2006-204294
PTL 3: JP-A-2006-34206
PTL 4: JP-A-4-75594
PTL 5: JP-A-8-33496

Non Patent Literature

NPL 1: *Cellulase*, issued from Kodansha Scientific, p. 97-104, 1987

DISCLOSURE OF INVENTION

Technical Problem

The invention aims to provide a mutant of a cellulase-producing microorganism which produces a cellulase capable of preferentially producing a cello-oligosaccharide during the selective production of the cello-oligosaccharide through enzymolysis of a cellulosic material in the presence of the cellulase, a method for producing the cellulase and a method for producing a cello-oligosaccharide using the cellulase.

Solution to Problem

The present inventors have prepared strains of a cellulase-producing microorganism in which a main β-glucosidase, main cellobiohydrolase genes and a main endoglucanase gene were knocked out by genetic engineering and found that cello-oligosaccharides can be produced highly selectively from a cellulosic material when the cellulases produced by the strains are used. The present invention has been thus completed.

That is, the invention is as follows.

1. A mutant of a cellulase-producing microorganism, wherein a cellobiohydrolase gene and a β-glucosidase gene are disrupted.
2. The mutant according to the above item 1, wherein the cellobiohydrolase genes are a gene belonging to glycoside hydrolase family (GHF) 6 and a gene belonging to GHF7, and the β-glucosidase gene is a gene belonging to GHF1 or GHF3.

3. The mutant according to the above item 2, wherein the β-glucosidase gene is a gene belonging to GHF3.
4. The mutant according to the above item 1, wherein an endoglucanase gene is further disrupted.
5. The mutant according to the above item 4, wherein the endoglucanase gene is a gene belonging to GHF7.
6. The mutant according to any one of the above items 1 to 5, wherein the cellulase-producing microorganism is a microorganism belonging to *Trichoderma*.
7. The mutant according to the above item 6, wherein the microorganism belonging to *Trichoderma* is one selected from the group consisting of *Trichoderma reesei, Trichoderma viride, Trichoderma atroviride* and *Trichoderma longibrachiatum*.
8. The mutant according to the above item 7, wherein the microorganism belonging to *Trichoderma* is *Trichoderma reesei*.
9. The mutant according to the above item 8, wherein the cellobiohydrolase genes are cbh1 gene and cbh2 gene, and the β-glucosidase gene is bgl1 gene.
10. The mutant according to the above item 8 or 9, wherein the endoglucanase gene is egl1 gene.
11. A method for producing a cellulase characterized in that a cellulase is produced by culturing the mutant according to any one of the above items 1 to 10.
12. A method for producing a cello-oligosaccharide containing a step of decomposing a cellulosic material using a cellulase produced by the mutant according to any one of the above items 1 to 10.
13. A method for producing a mutant of a cellulase-producing microorganism, containing disrupting a cellobiohydrolase gene and a β-glucosidase gene.

Advantageous Effects of Invention

β-Glucosidase genes and cellobiohydrolase genes have been thought to be essential for the existence of a cellulase-producing microorganism, and it has been thought to be difficult to obtain a cellulase-producing microorganism when these genes are disrupted. In the invention, it was found that a cellulase-producing microorganism can live and grow even when a β-glucosidase gene and a cellobiohydrolase gene have been disrupted, and it was also found that the cellulase that the cellulase-producing microorganism produces can produce a cello-oligosaccharide composed of three or more monosaccharide units highly selectively, efficiently and easily.

Since a main β-glucosidase gene of the mutant cellulase-producing microorganism of the invention has been disrupted, the β-glucosidase activity of the cellulase that the mutant produces is decreased significantly. Also, since a main cellobiohydrolase gene of the mutant has been disrupted, a cello-oligosaccharide composed of three or more monosaccharide units can be produced highly selectively when the cellulase produced by the mutant is used.

In addition to a main β-glucosidase gene and a main cellobiohydrolase gene, a main endoglucanase gene of the mutant has been disrupted, and thus a cello-oligosaccharide composed of three or more monosaccharide units can be produced with higher selectivity.

Therefore, the cellulase produced by the mutant cellulase-producing microorganism of the invention can produce a cello-oligosaccharide highly selectively from a cellulosic material.

Furthermore, when the cellulase produced by the mutant cellulase-producing microorganism of the invention is used, a cello-oligosaccharide can be produced highly selectively from a cellulosic material without any complicated purification step and at a low cost.

BRIEF DESCRIPTION OF DRAWINGS

FIG. 6 shows schematic diagrams explaining the pyr4 selection marker.

Figure 12:
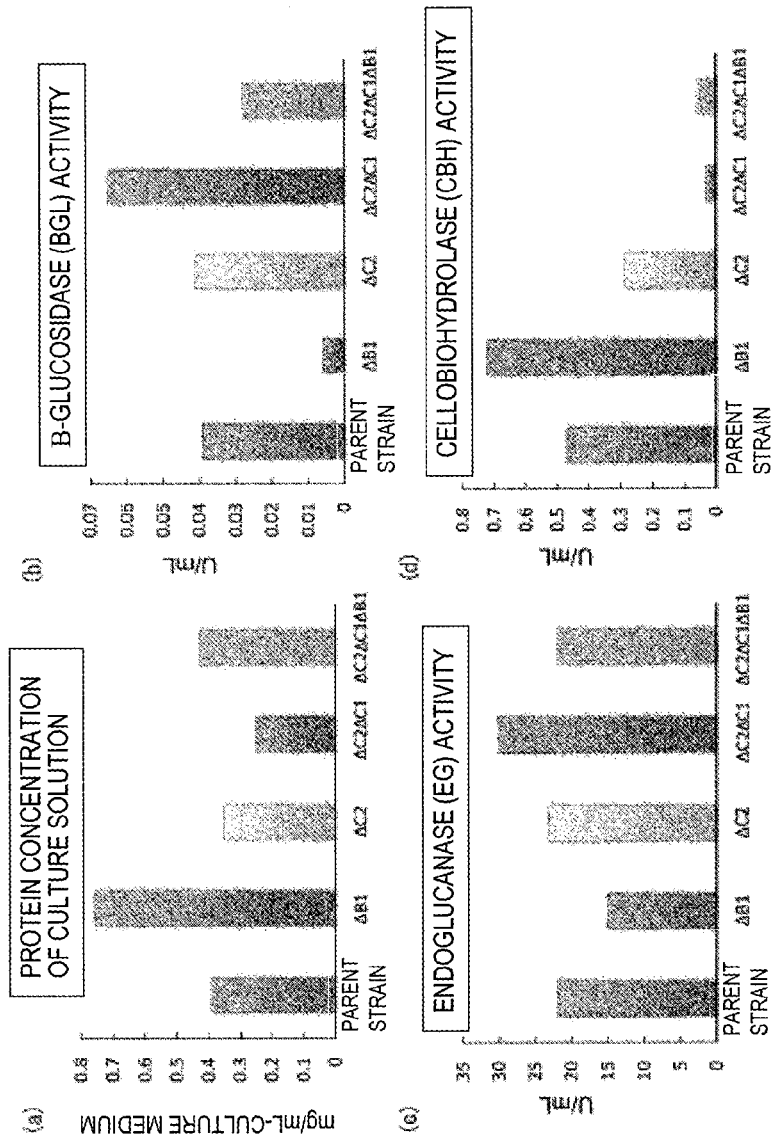

Panel (a) of FIG. 12 shows the protein concentrations of the culture solutions of the transformants produced in the Examples. Panels (b) to (d) of FIG. 12 show the results of evaluation of the activities of the enzymes obtained from the transformants produced in the Examples.

Figure 13:
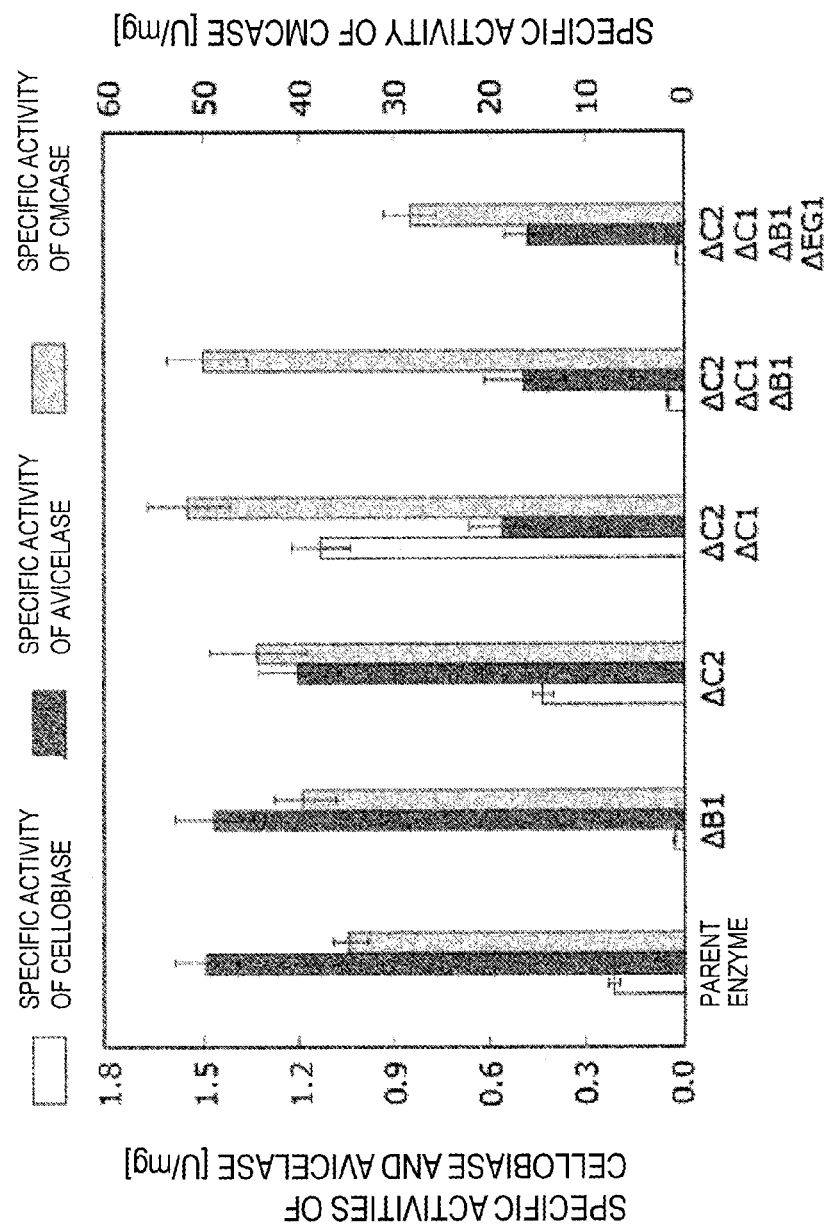

FIG. 13 shows the results of evaluation of the activities of the enzymes obtained from the transformants produced in the Examples.

Figure 14:
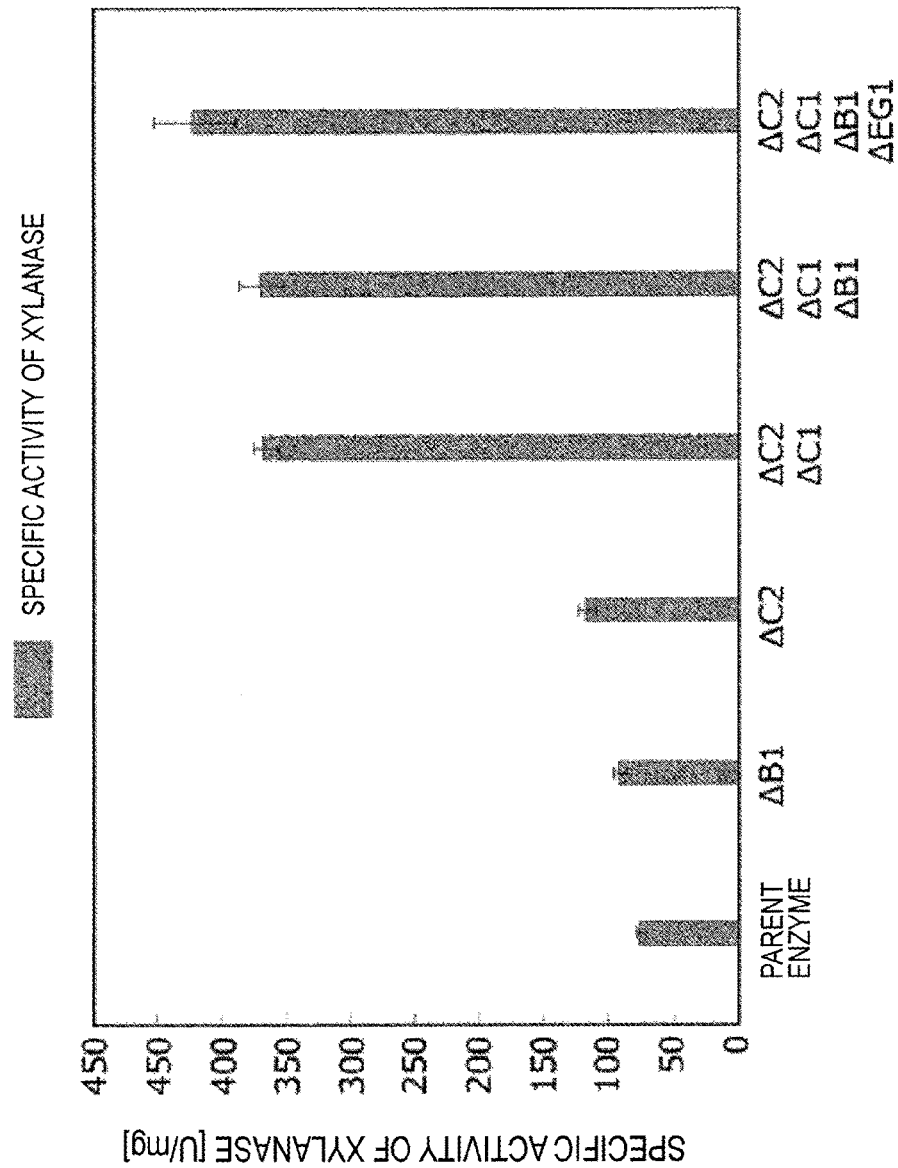

FIG. 14 shows the results of evaluation of the xylanase activities of the enzymes obtained from the transformants produced in the Examples.

Figure 15:
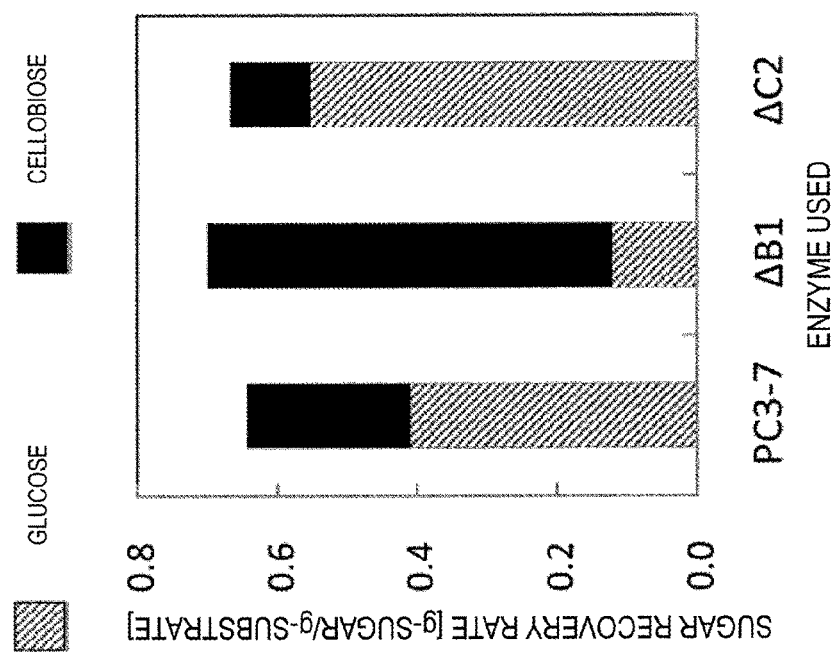

FIG. 15 shows the results of evaluation of the oligosaccharide productivity using enzymes obtained from single enzyme-knockout strains.

Figure 16:
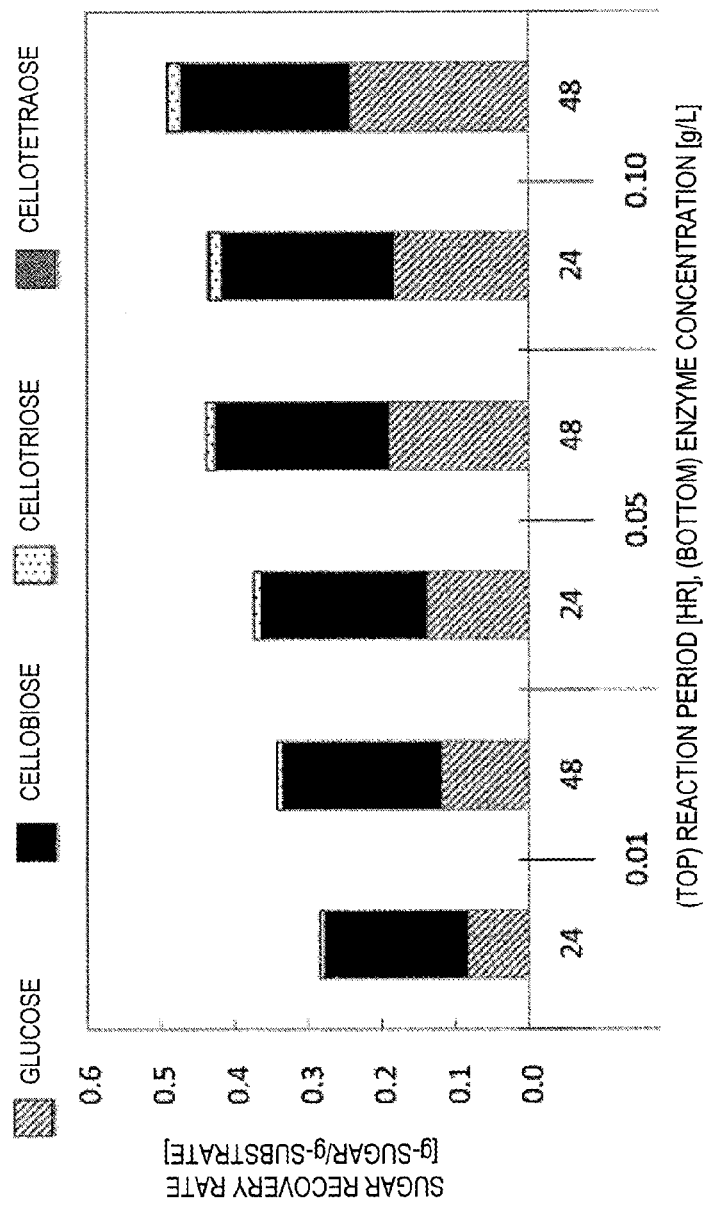

FIG. 16 shows the results of evaluation of the oligosaccharide productivity using enzymes obtained from a triple enzyme gene-knockout strain (ΔC2ΔC1ΔB1).

Figure 17:
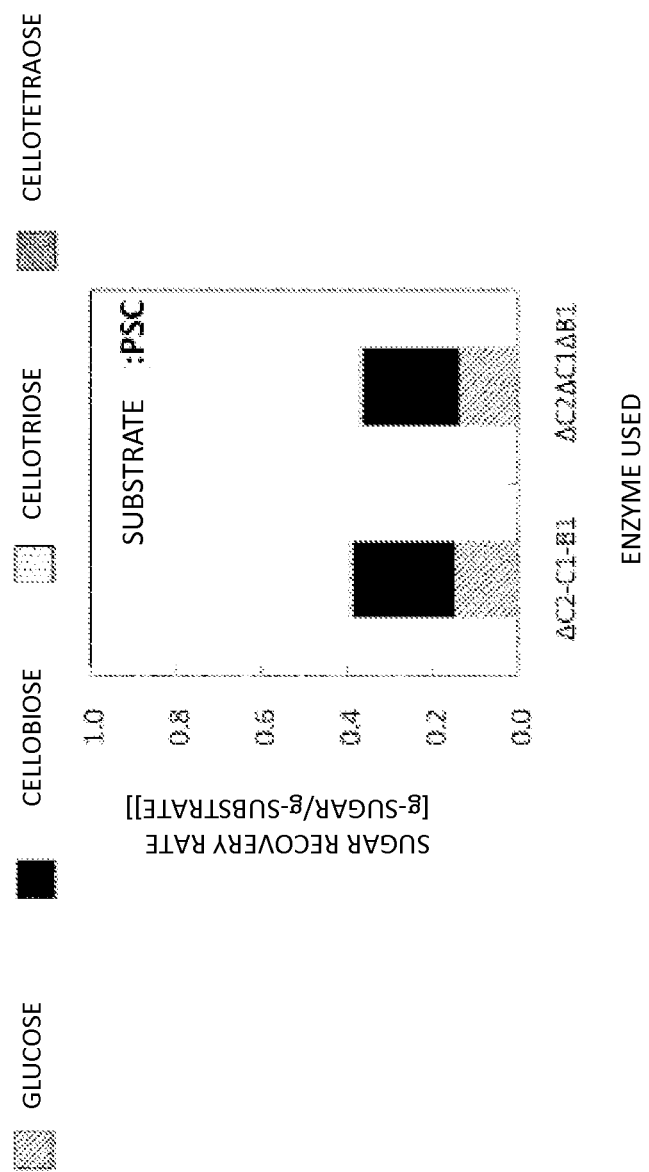

FIG. 17 shows the results of evaluation of the oligosaccharide productivity using fractionated enzymes prepared by removing CBHI, CBHII and β-glucosidase 1 from the cellulases obtained from the parent strain and using cellulases obtained from a cbh1-, cbh2- and bgl1-knockout strain (ΔC2ΔC1ΔB1, a triple enzyme gene-knockout strain).

Figure 18:
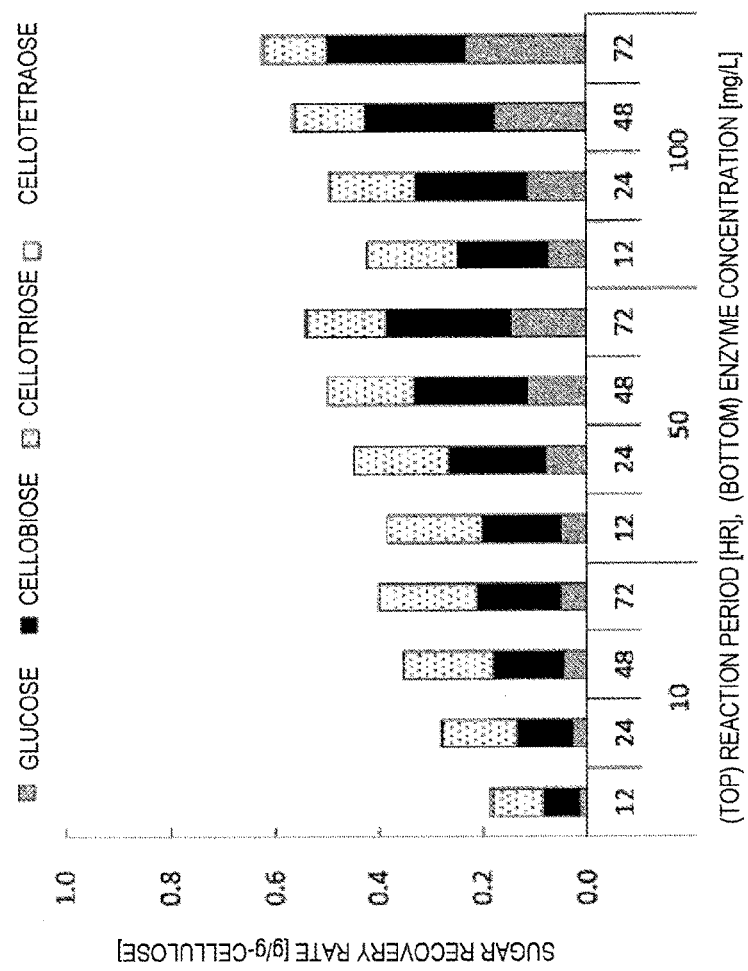

FIG. 18 shows the results of evaluation of the oligosaccharide productivity using enzymes obtained from a quadruple enzyme gene-knockout strain (ΔC2ΔC1ΔB1ΔEG1).

Figure 19:
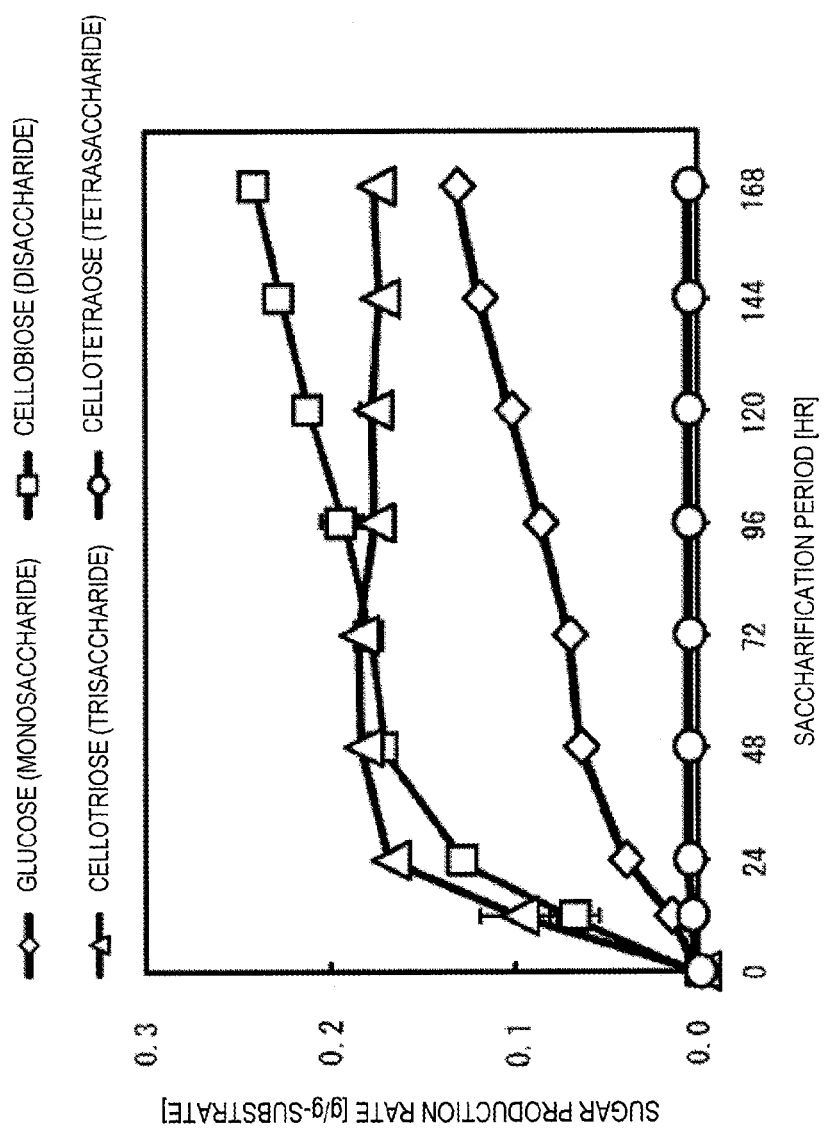

FIG. 19 shows the results of evaluation of the oligosaccharide productivity and the influence of the saccharification period using enzymes obtained from a quadruple enzyme gene-knockout strain.

DESCRIPTION OF EMBODIMENTS

1. Mutant of Cellulase-Producing Microorganism

The invention relates to a mutant of a cellulase-producing microorganism in which a cellobiohydrolase gene, a β-glucosidase gene and an endoglucanase gene have been disrupted. Examples of the cellulase-producing microorganism include microorganisms described in *Cellulase* (issued from Kodansha Scientific (1987)) and *Cellulose No Jiten* (issued from Asakura Publishing Co., Ltd. (2000)), such as those of *Trichoderma, Acremonium, Aspergillus, Bacillus, Pseudomonas, Penicillium, Aeromonus, Irpex, Sporotrichum* and *Humicola*. Microorganisms belonging to *Trichoderma* are preferable among the examples.

Examples of microorganisms belonging to *Trichoderma* include *Trichoderma aggressivum, Trichoderma atroviride, Trichoderma asperellum, Trichoderma aureoviride, Trichoderma austrokoningii, Trichoderma brevicompactum, Trichoderma candidum, Trichoderma caribbaeum varaequatoriale, Trichoderma caribbaeum var. Caribbaeum, Trichoderma catoptron, Trichoderma cremeum, Trichoderma ceramicum, Trichoderma cerinum, Trichoderma chlorosporum, Trichoderma chromospermum, Trichoderma cinnamomeum, Trichoderma citrinoviride, Trichoderma crassum, Trichoderma cremeum, Trichoderma dingleyeae, Trichoderma dorotheae, Trichoderma effusum, Trichoderma erinaceum, Trichoderma estonicum, Trichoderma fertile, Trichoderma gelatinosus, Trichoderma ghanense, Trichoderma hamatum, Trichoderma harzianum, Trichoderma helicum, Trichoderma intricatum, Trichoderma konilangbra, Trichoderma koningii, Trichoderma koningiposis, Trichoderma longibrachiatum, Trichoderma longipile, Trichoderma minutisporum, Trichoderma oblongisporum, Trichoderma ovalisporum, Trichoderma petersenii, Trichoderma phyllostahydis, Trichoderma piluliferum, Trichoderma pleuroticola, Trichoderma pleurotum, Trichoderma polysporum, Trichoderma pseudokoningii, Trichoderma pubescens, Trichoderma reesei, Trichoderma rogersonii, Trichoderma rossicum, Trichoderma saturnisporum, Trichoderma sinensis, Trichoderma sinuosum, Trichoderma* sp. MA 3642, *Trichoderma* sp. PPRI 3559, *Trichoderma spirale, Trichoderma stramineum, Trichoderma strigosum, Trichoderma stromaticum, Trichoderma surrotundum, Trichoderma taiwanense, Trichoderma thailandcum, Trichoderma thelephorucolum, Trichoderma theobromicola, Trichoderma tomentosum, Trichoderma, Trichoderma, Trichoderma velutinum, Trichoderma virens, Trichoderma viride* and *Trichoderma viridescens*. From a viewpoint of secretory productivity of cellulases, *Trichoderma reesei, Trichoderma viride, Trichoderma atroviride* or *Trichoderma longibrachiatum* is preferable among the examples, and *Trichoderma reesei* is more preferable.

Example strains of *Trichoderma reesei* include *Trichoderma reesei* QM9414 and *Trichoderma reesei* PC-3-7.

Figure 1:
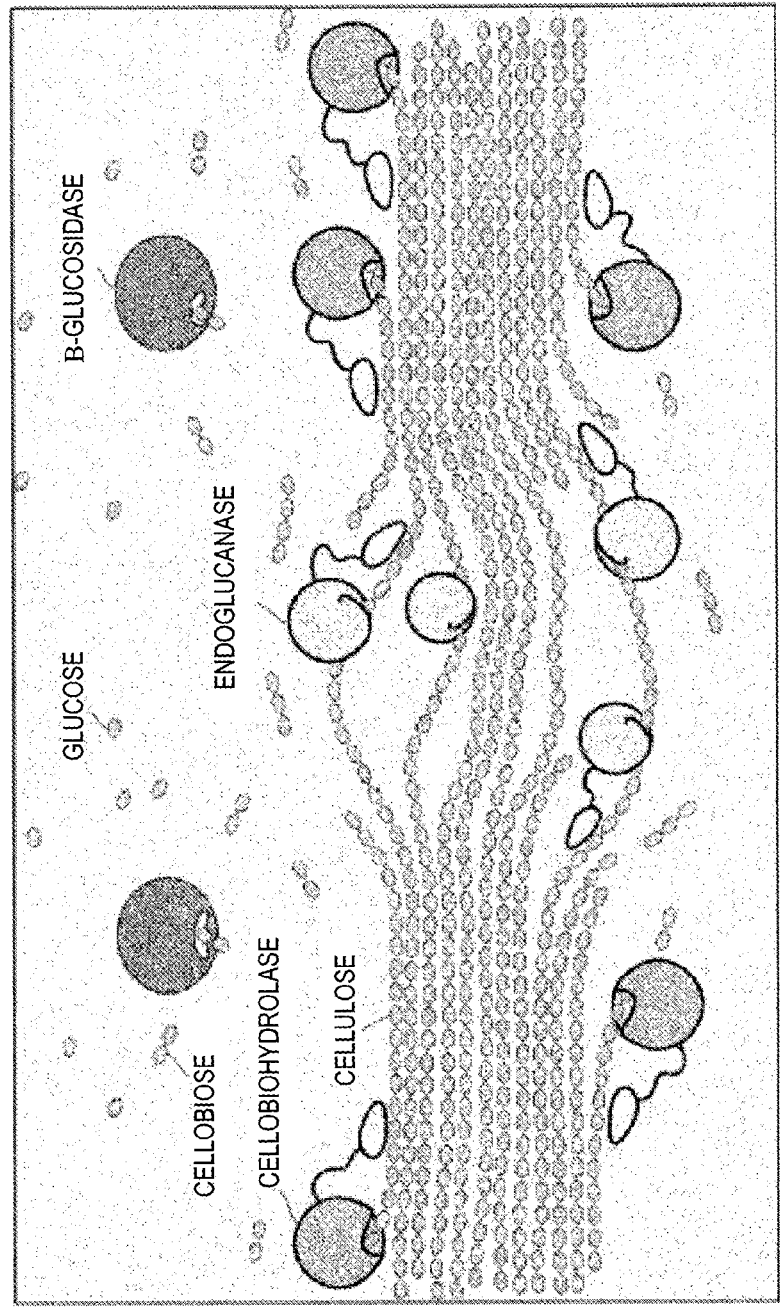
FIG. 1 shows a schematic diagram of the mechanism of decomposition of cellulose by cellulases.
Figure 2:
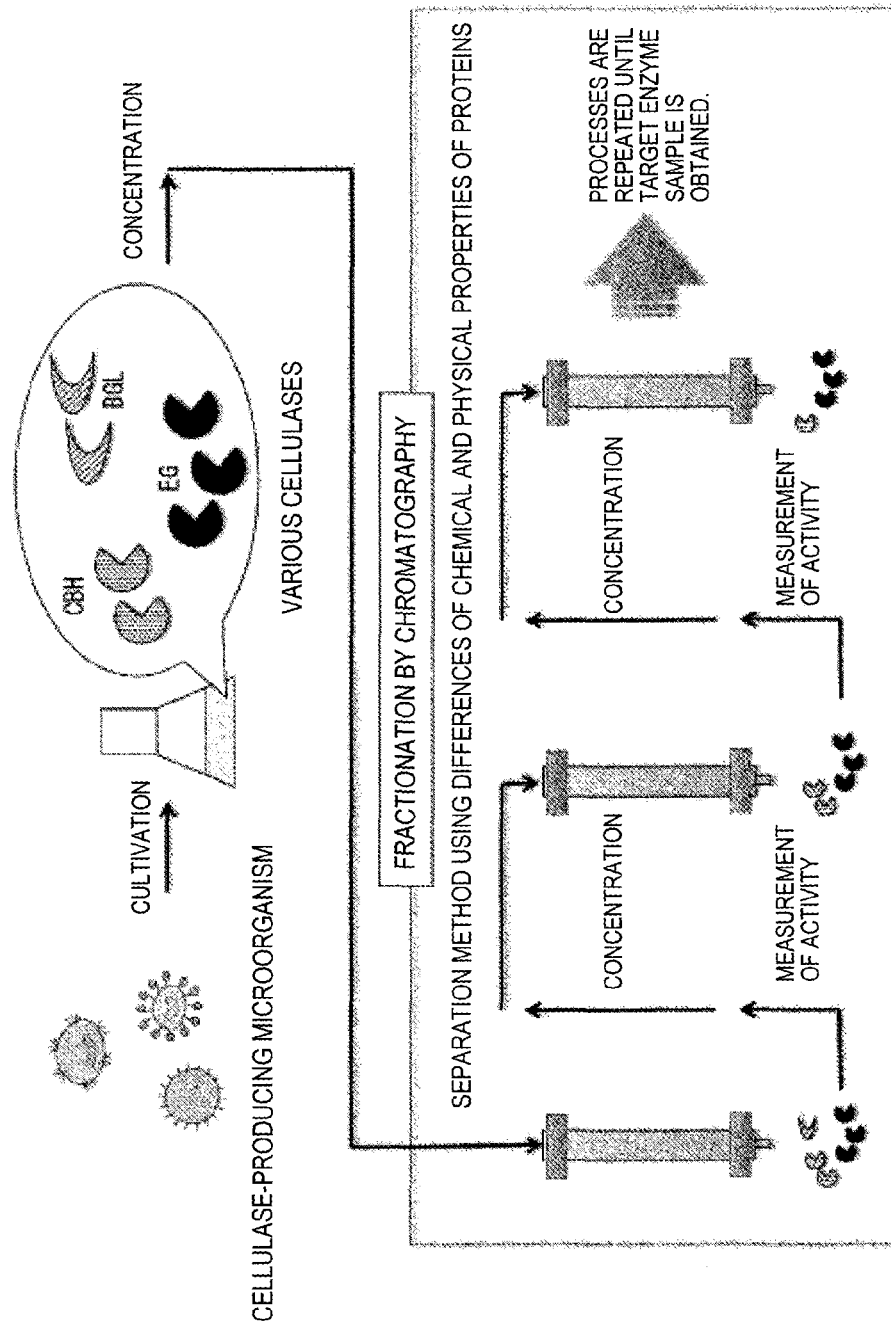
FIG. 2 shows a schematic diagram of enzyme fractionation using fractionation by chromatography.
Figure 3:
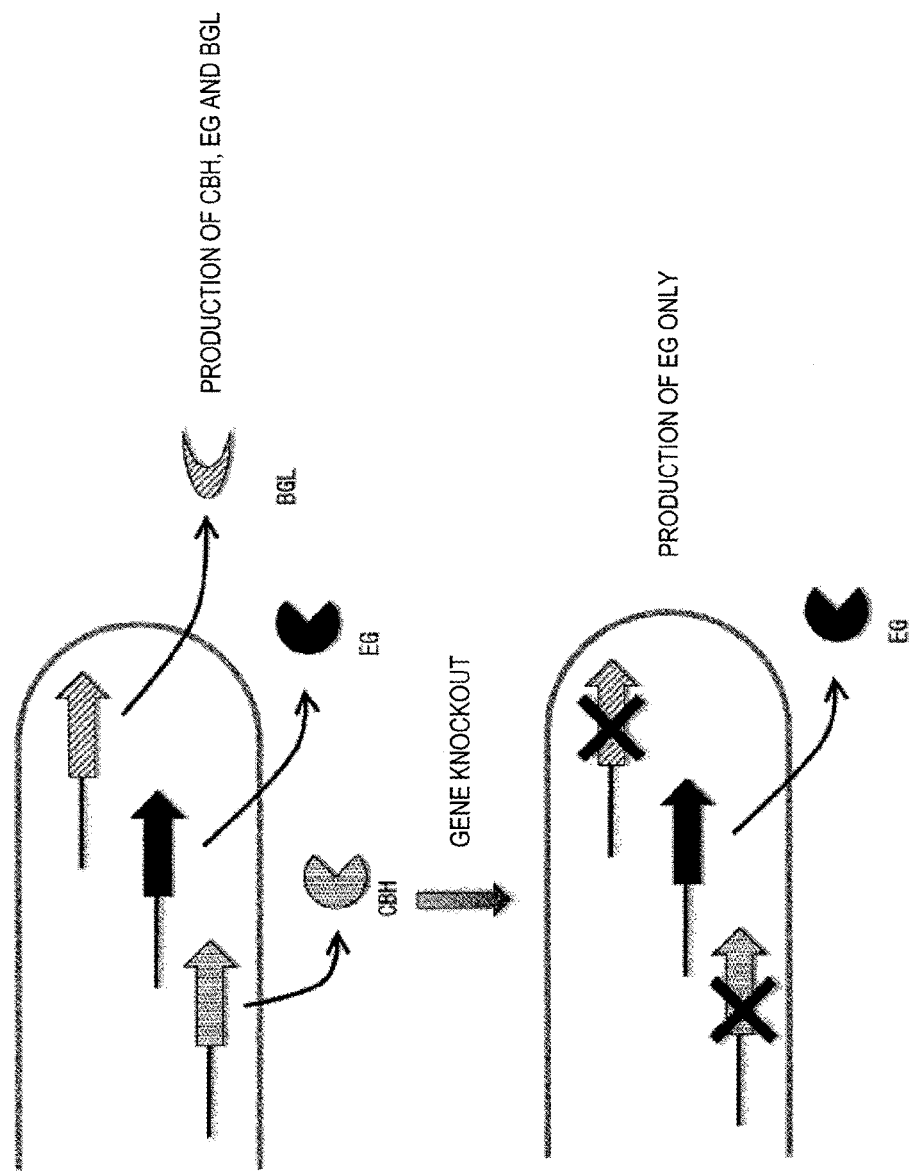
FIG. 3 shows a schematic diagram of a method for producing a mutant which produces an endoglucanase only from a cellulase-producing microorganism by disrupting its genes.

The genes that are disrupted in the invention are a cellobiohydrolase gene and β-glucosidase gene. As shown in FIG. 3, when a cellobiohydrolase gene and a β-glucosidase gene of a cellulase-producing microorganism are disrupted, a mutant which produces an endoglucanase only can be obtained. Complete removal of the enzyme components is possible using the mutant, as compared to enzyme fractionation, and a cello-oligosaccharide can be produced efficiently.

By further disrupting an endoglucanase gene, a cello-oligosaccharide composed of three or more monosaccharide units can be produced with higher selectivity.

The cellobiohydrolase genes are preferably a gene belonging to glycoside hydrolase family [GHF (www.cazy.org/Glycoside-Hydrolases.html)] 6 and a gene belonging to GHF7. The .beta.-glucosidase gene is preferably a gene belonging to GHF1 or GHF3, more preferably a gene belonging to GHF3.

Figure 4:
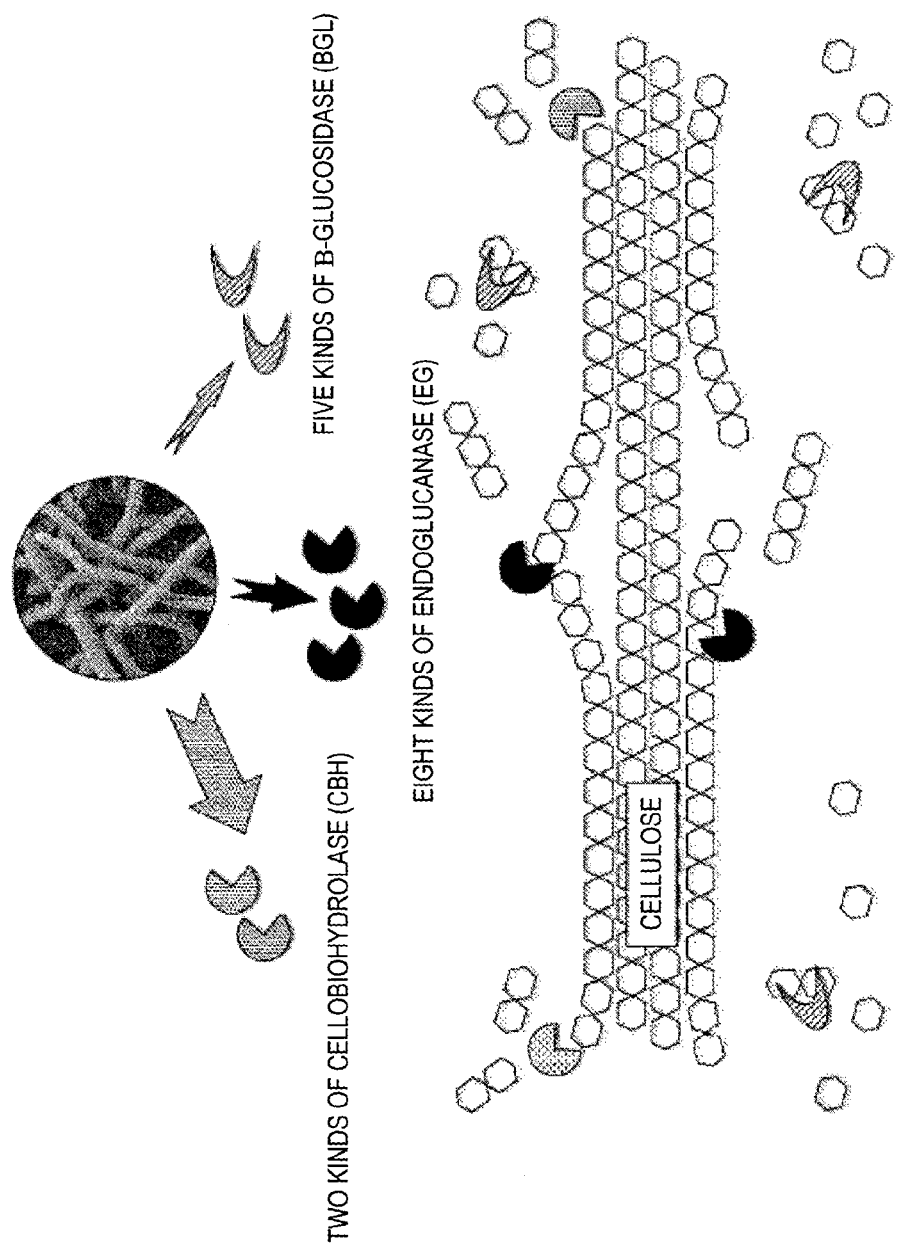
FIG. 4 shows a schematic diagram of the cellulose degrading enzymes produced by *Trichoderma reesei*.

The cellulose degrading enzymes that *Trichoderma reesei* produces are shown in FIG. 4. As shown in FIG. 4, the cellulose degrading enzymes of *Trichoderma reesei* include at least two kinds of cellobiohydrolase (CBHI and CBHII), eight kinds of endoglucanase (EGI to EGVIII) and 10 kinds of β-glucosidase (BGLI, BGLII, Cel1b and Cel3b to Cel3h). Among them, five kinds of β-glucosidase (BGLI, Cel3b, Cel3e, Cel3f and Cel3g) are secreted and released to the outside the microorganism.

Among the two kinds of cellobiohydrolase (CBHI and CBHII) of *Trichoderma reesei*, CBHI (Cel7a) belongs to GHF7 while CBHII (Cel6a) belongs to GHF6. Among the eight kinds of endoglucanase (EGI to EGVIII), EGI (Cel7b) belongs to GHF7, EGII (Cel5a) belongs to GHF5, EGIII (Cell2a) belongs to GHF12, EGIV (Cel61a) belongs to GHF61, EGV (Cel45a) belongs to GHF45, EGVI (Cel74a) belongs to GHF74, EGVII (Cel61b) belongs to GHF61, and EGVIII (Cel5b) belongs to GHF5. Among the 10 kinds of p-glucosidase (BGLI, BGLII, Cell band Cel3b to Cel3h), BGLI (Cel3a) belongs to GHF3, BGLII (Cel7a) belongs to GHF1, Cell b belongs to GHF1, and Cel3b to h belong to GHF3.

Figure 5:
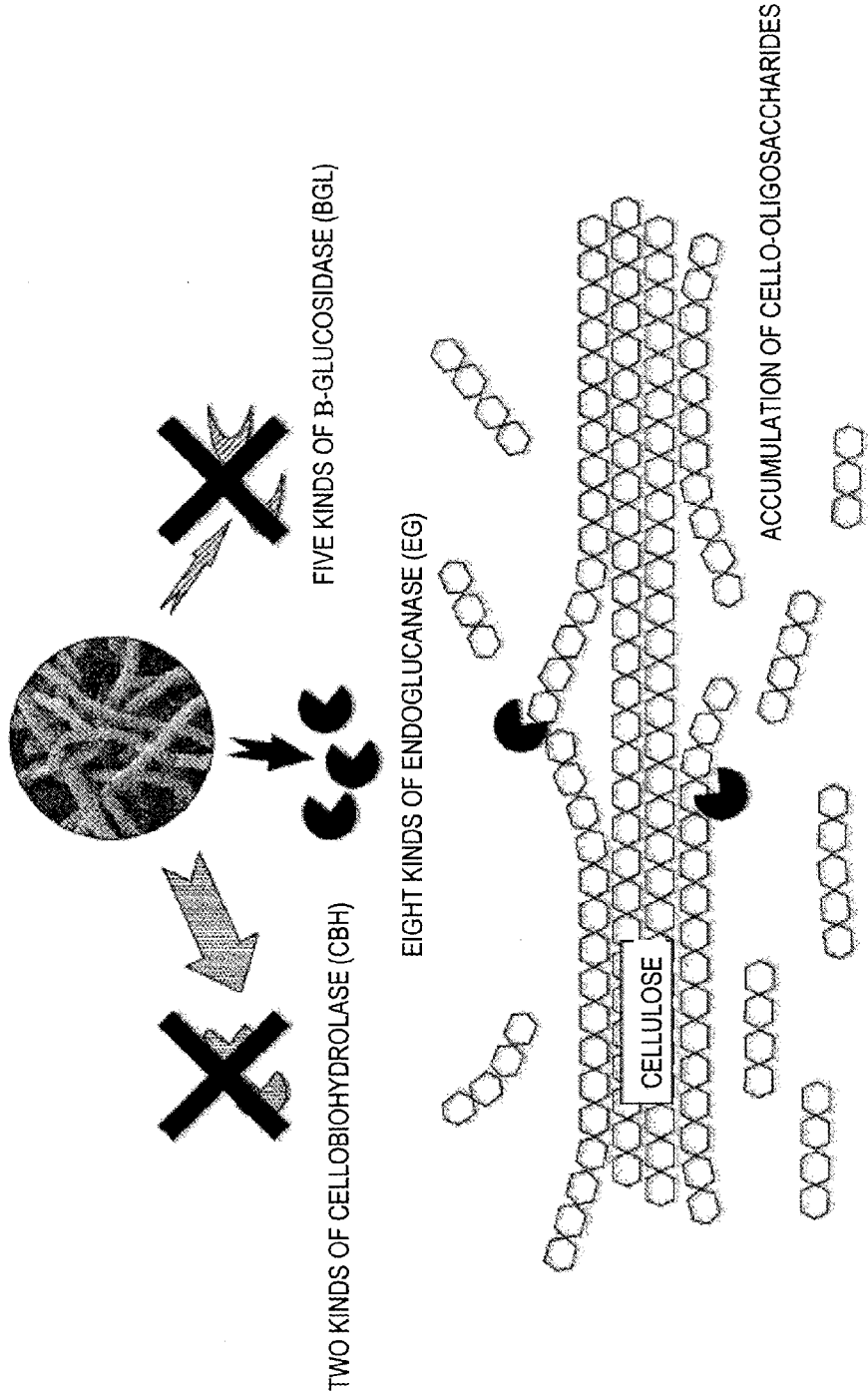
FIG. 5 shows a schematic diagram of a method for producing a cello-oligosaccharide by disrupting genes of a cellulase-producing microorganism.

When the microorganism belonging to *Trichoderma* is *Trichoderma reesei*, it is preferable that the genes shown in Table 1 (cellobiohydrolase and .beta.-glucosidase genes) are disrupted (FIG. 5). Furthermore, an endoglucanase is preferably disrupted. In this regard, the names, numbers, functions and the like of the genes in Table 1 are described based on GenBank and JGI (*Trichoderma reesei*) (genome.jgi-psf.org/Trire2/Trire2.home.html).

TABLE 1

| Gene Name | Gene No. | Explanation of Function | Reference | SEQ ID NO |
|---|---|---|---|---|
| cbh1 | E00389 | Cellobiohydrolase | 1 | 1 |
| cbh2 | M16190 | Cellobiohydrolase | 2 | 2 |
| bgl1 | U09580 | β-Glucosidase | 3 | 3 |
| cel3b | 121735 | β-Glucosidase | 4 | 4 |
| cel3e | 76227 | β-Glucosidase | 4 | 5 |
| Estimated bgl (cel3f) | 47268 | β-Glucosidase | 4 | 6 |
| Estimated bgl (cel3g) | 104797 | β-Glucosidase | 4 | 7 |
| egl1 | M15665 | Endoglucanase | 5 | 9 |

Reference 1: JP 1985149387-A/1
Reference 2: Gene 51(1), 43-52 (1987)
Reference 3: Thesis (1993) Mikrobielle Biochemie, Inst. biochem. Technol
Reference 4: Nat Biotechnol. 26, 553-560 (2008)
Reference 5: *Homology between cellulase genes of Trichoderma reeseikoron complete nucleotide sequence of the endoglucanase I gene*, Penttila, M., Lehtovaara, P., Nevalainen, H., Bhikhabhai, R. and Knowles, J., Gene 45(3), 253-263 (1986)

In the invention, for the purpose of producing a cello-oligosaccharide composed of three or more monosaccharide units highly selectively, three or more of the eight genes are preferably disrupted. Four or more of the genes are more preferably disrupted, and five or more of the genes are further preferably disrupted. More specifically, it is preferable to disrupt at least three of the genes, namely cbh1, cbh2 and bgl1. It is further preferable to disrupt four of the genes, namely cbh1, cbh2, bgl1 and egl1. Mutants in which these genes have been disrupted can be produced according to the method described in Mol. Gen. Genet. 241 (5-6), 523-530 (1993).

The genes described in Table 1 may be, for example, genes which have the respective nucleotide sequences of the genes having deletion, substitution or addition of one or several nucleotides and which have the same functions as those of the respective genes. Moreover, genes which have the same functions as those of the respective genes shown in Table 1 and/or which have nucleotide sequences with a homology of 70% or more, preferably 80% or more, more preferably 90% or more, further preferably 95% or more, particularly preferably 98% or more to the nucleotide sequences of the respective genes in Table 1 are believed to correspond to the genes shown in Table 1, and these genes are also included in the invention as the genes which may be disrupted.

The genes can be inactivated by a method of inserting another DNA fragment into the genes, a method of introducing a mutation into the transcription/translation start sites of the genes and the like, but it is more preferable to physically delete the target genes.

Processes for disrupting a gene or a group of genes include a method of systematically disrupting the target gene(s) shown in Table 1, as well as a method of introducing random deletion or inactivating mutation into the gene(s) and then evaluating the protein productivity and analyzing the gene(s) by suitable methods.

In order to disrupt a target gene, a method by homologous recombination may be used for example. In other words, a target gene in the genome of the parent strain can be interrupted and inactivated through homologous recombination of a part of the target gene, by cloning a DNA fragment containing a part of the target gene using a suitable plasmid vector and transforming the cells of the parent strain with the obtained circular recombinant plasmid.

In another method, a target gene in the genome can be replaced with a disrupted gene fragment by: constructing a mutant target gene to which an inactivation mutation is introduced by nucleotide substitution, nucleotide insertion or the like, a linear DNA fragment which contains the outer regions of the target gene but does not contain the target gene or the like, by a method such as PCR: transforming the cells of the parent strain with the mutant target gene or the linear DNA fragment: and thus inducing homologous recombination by double crossing over at one site in the outer regions of the mutation site introduced to the target gene in the parent strain genome or at one site in the outer regions of the target gene.

In particular, with respect to a method for disrupting a target gene of a cellulase-producing microorganism through homologous recombination, several examples have already been reported (marker recycling method and the like), and the mutant cellulase-producing microorganism of the invention can be obtained according to such a method.

Example methods for deleting or inactivating a gene at random include a method where homologous recombination similar to those of the above methods is induced using a randomly cloned DNA fragment and a method where the parent strain is irradiated with γ ray or the like.

As a more specific example, a method for producing multiple gene- (cbh1-, cbh2- and bgl1-) knockout strains using marker recycling method [Curr. Genet., 48(3), 204-211 (2005)] is explained below, but the method for disrupting genes of the invention is not limited to the following method.

The gene pyr4 (SEQ ID NO:8) is a selection marker gene, and as shown in FIGS. 6 (a) and (b), a pyr4$^+$ strain can grow without the addition of uridine to the culture medium while a pyr4$^-$ strain (a pyr4-knockout strain) is resistant to 5-fluoroorotic acid (5-FOA) and is an uridine auxotrophic strain.

Figure 7:
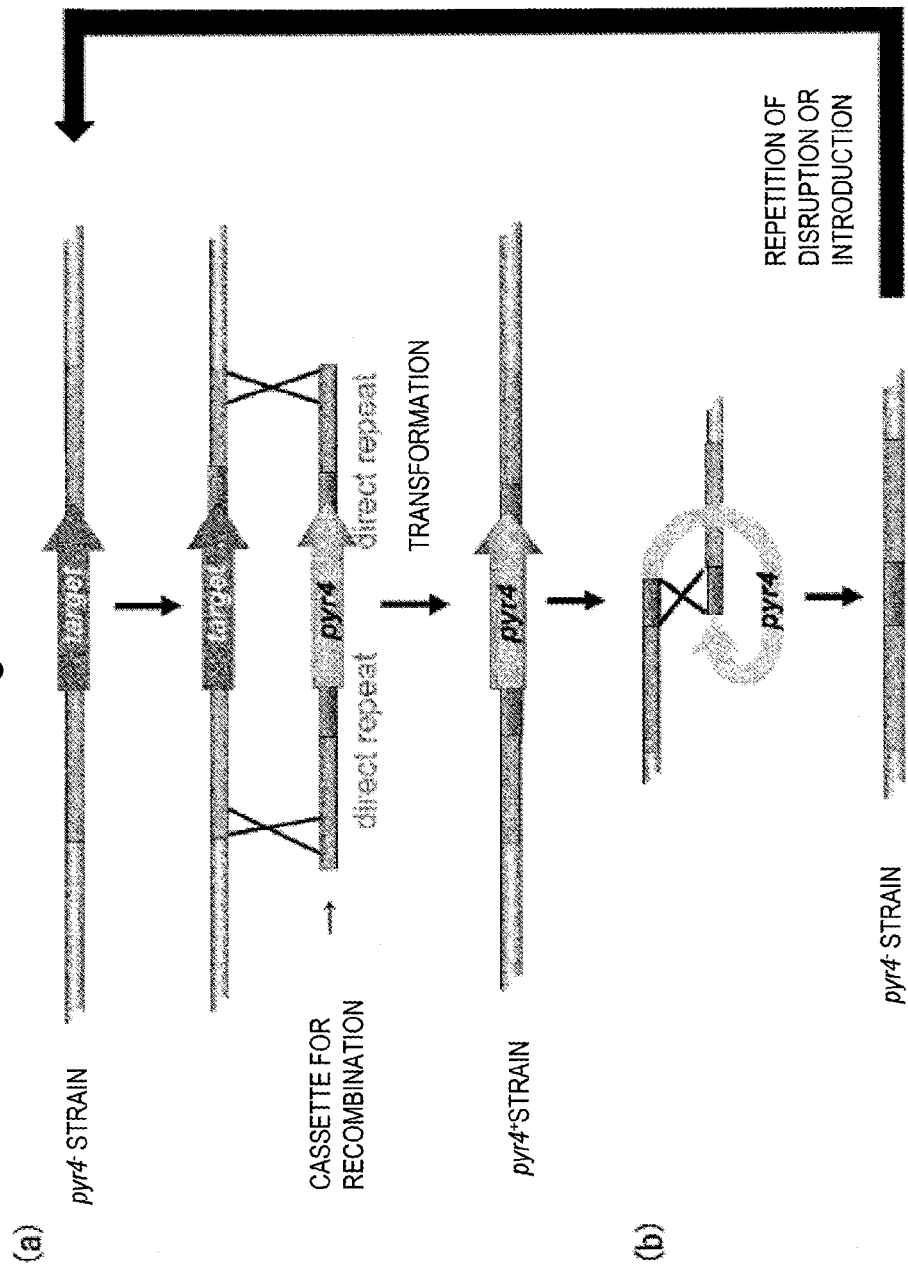
FIG. 7 shows schematic diagrams of marker recycling method using a pyr4-knockout strain.
Figure 8:
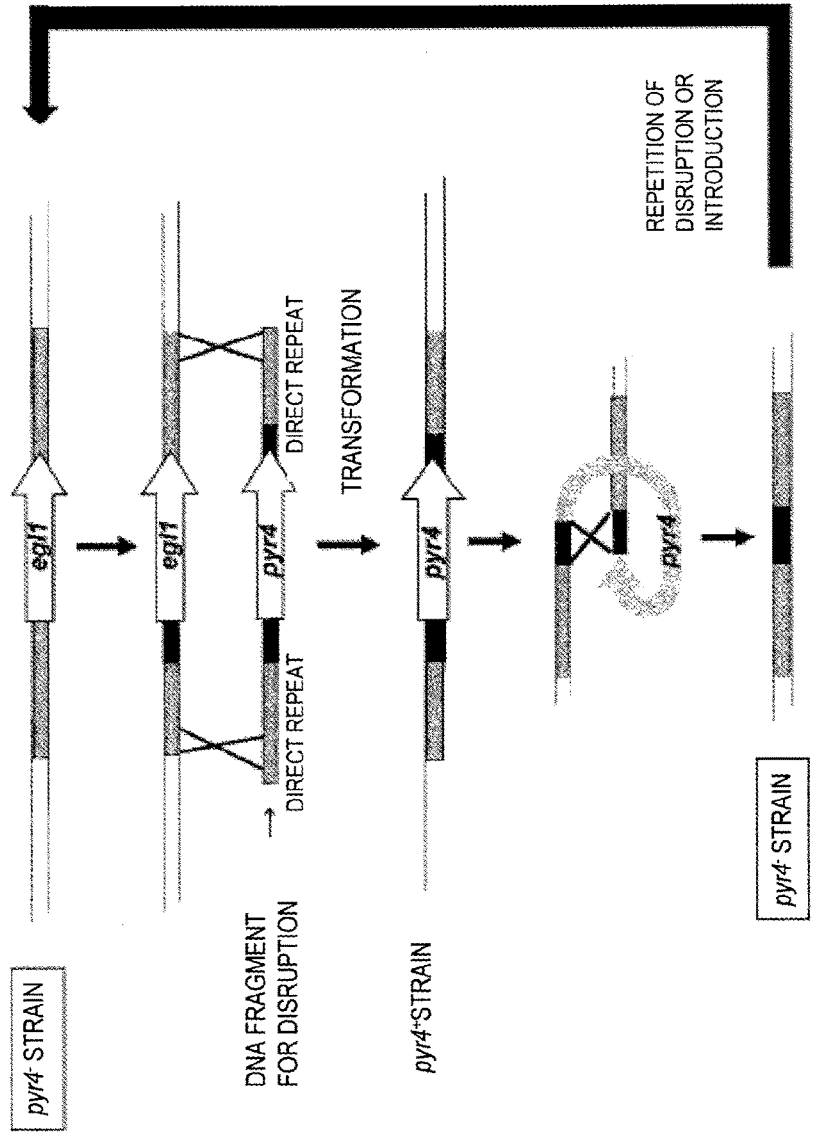
FIG. 8 shows a schematic diagram of the disruption of egl1 gene using a pyr4-knockout strain.

Marker recycling method using a pyr4-knockout strain is explained referring to FIG. 7. A cassette for recombination in which the target gene has been replaced with pyr4 and which has direct repeats is introduced into an uridine auxotrophic strain (pyr4$^-$) obtained by gene disruption by gene targeting using the 5-FOA resistance as an index, and transformants which grow in a culture medium containing no uridine are obtained [FIG. 7 (a)]. From the obtained transformants, a strain having one copy of the disruption cassette inserted at the target site through double crossover is selected by Southern blotting analysis. Then, spores of the obtained strain are applied on a culture medium containing 5-FOA, and a colony which has regained the resistance to 5-FOA after pyr4 has been removed through intramolecular homologous recombination and which thus grows on the culture medium is used as a target gene-knockout strain [FIG. 7 (b)]. The step is repeated to disrupt multiple genes, and the mutant cellulase-producing microorganism of the invention can be obtained. An example explaining the case where the target gene is egl1 gene is shown in FIG. 8.

Various cellulose materials such as Avicel, powder of filter paper, and biomass containing cellulose are used as the carbon sources for the cultivation. Examples of the nitrogen source are polypeptone, ammonium sulfate, broth, corn steep liquor (CSL) and soybean cake.

In addition, a component necessary for producing the target cellulase may be added to the culture medium. Moreover, the addition of a xylan component to the culture medium can increase the production of xylanase.

For the cultivation of the strains, various culture methods such as shake culture, rotary culture, rotary shake culture, static culture and continuous culture may be employed, but shake culture or rotary culture is preferable. The cultivation temperature is generally from 20° C. to 35° C., preferably from 25° C. to 31° C., and the cultivation period is generally from 4 to 10 days, preferably from 4 to 9 days.

The cellulase thus produced by a mutant can be recovered from the extracellular part of the mutant. The cellulase can be measured by analyzing the cell lysate or the supernatant sample of the culture medium directly by sodium dodecyl sulfate-polyacrylamide gel electrophoresis (SDS-PAGE) and Western blotting, which are known in this technical field.

The cellulase produced during the cell cultivation is secreted in the culture medium and purified or separated for example by removing unnecessary components from the cell culture. Examples of the method for purifying the cellulase include affinity chromatography, ion exchange chromatography, hydrophobic interaction chromatography, ethanol precipitation, reverse-phase HPLC, cation exchange chromatography for example on silica or DEAE, chromatofocusing, SDS-PAGE, ammonium sulfate precipitation and gel filtration. One of these methods may be used alone, or a combination of the methods may be used.

2. Method for Producing Cello-Oligosaccharide

The method for producing a cello-oligosaccharide through enzymolysis of cellulose using the cellulase may be a known method and is not particularly restricted. In an example method, a cellulosic material is suspended as a substrate in an aqueous medium, followed by adding the cellulase produced according to the method of the invention, and saccharification is carried out by heating while stirring or shaking the mixture.

The reaction conditions of the method such as the suspending method, the stirring method, the method and the order for adding the cellulase and the substrate and their concentrations may be suitably adjusted so that the yield of the obtained cello-oligosaccharide becomes higher. The pH and the temperature of the reaction solution should be within ranges in which enzymes are not deactivated, and in general, the temperature may be within the range from 5 to 95° C. and the pH may be within the range from 1 to 11 when the reaction is carried out under the normal pressure.

The cellulosic material may be a water-soluble or water-insoluble material and may be derived from a plant or an animal. Examples of the animals and plants producing the cellulosic material include wood, bamboo, wheat straw, rice straw, corncob, cotton, ramie, bagasse, kenaf, beet, ascidians and bacterial cellulose.

In addition to natural cellulosic material produced by the animals and plants, regenerated cellulosic materials obtained by once chemically/physically dissolving or swelling a natural cellulosic material and then regenerating the substance and cellulose derivative-based substances obtained by chemically modifying a cellulosic material may be used. For industrial purposes, the cellulosic material may be any of natural cellulosic materials such as pulp, cellulose powder and crystalline cellulose, regenerated cellulose such as rayon, various regenerated cellulosic materials such as alkaline cellulose and phosphoric acid-swollen cellulose (PSC), and various cellulose derivatives such as carboxymethylcellulose (CMC) sodium salt.

In this regard, however, in order to use the cello-oligosaccharide obtained for medicines, foods or cosmetics, a natural cellulosic material is preferably used. One kind of the cellulosic materials may be used as the starting material, or a mixture of two or more kinds may be used.

The production process of a cello-oligosaccharide through enzymolysis of cellulose using the cellulase may be batch process or continuous process. In order to avoid the product inhibition due to cellobiose during the enzymolysis, it is preferable from the viewpoint of increasing the productivity of the cello-oligosaccharide to keep the cellobiose concentration in the reaction system within a specific range so that the reaction is not influenced by the product inhibition of the cellulase.

Examples of the method for keeping the cellobiose concentration in the reaction system within a specific range are: a method in which produced cellobiose is removed from the reaction system by membrane filtration such as ultrafiltration or reverse osmosis filtration; a method in which an organic porous base material such as activated carbon and dry plant powder of bamboo, wood or the like, an inorganic porous base material such as silicon dioxide or the like is introduced into the reaction system, and cellobiose is adsorbed onto the base material; a method in which a cellulose substrate is immobilized in a column or the like, and a reaction solution containing the cellulase is made pass through the column or the like; and a method in which the cellulase is immobilized on a polymer or the like, and a reaction solution containing cellulose is made pass through the polymer or the like.

The aqueous solution which contains a cello-oligosaccharide as the main component and which is obtained by the enzymolysis can be subjected to purification treatment such as decolorization, desalination or enzyme removal if necessary. The purification method is not particularly restricted as long as it is a known method, but examples include activated carbon treatment, ion exchange resin treatment, chromatography treatment, filtration treatment such as microfiltration, ultrafiltration or reverse osmosis filtration and crystallization treatment. One of the methods may be used alone, or a combination of two or more of the methods may be used.

The aqueous solution containing a cello-oligosaccharide as the main component purified by the method may be used as it is but may be solidified by drying if necessary. The drying method is not particularly restricted as long as it is a known method, but for example, spray drying, freeze-drying, drum drying, thin film drying, shelf drying, pneumatic conveying drying, vacuum drying or the like may be used. One of the methods may be used alone, or a combination of two or more of the methods may be used.

As the medium for the cello-oligosaccharide during the purification and drying treatment, an organic solvent or the like may be used if necessary in addition to water. The organic solvent used here is not particularly restricted, but for example, those which are used in the steps for producing medicines, foods and additives thereof are preferable. Examples are those classified as solvents in *Japanese Pharmaceutical Excipients Directory* (issued from Yakuji Nippo Limited.), *Japanese Pharmacopoeia* and *Japan's Specifications and Standards for Food Additives* (both are issued from Hirokawa Shoten Co.). Water and the organic solvent may be each used alone, or two or more kinds may be used in combination. Also, the cello-oligosaccharide may be once dispersed in one kind of medium and then dispersed in a different medium after removing the first medium.

The form of the cello-oligosaccharide which has passed through the above steps is not particularly restricted, but for example, the cello-oligosaccharide may be used in the form of a solid, a suspension, an emulsion, syrup or a solution at room temperature. Examples of the solid cello-oligosaccharide include powder, granules, pellets, a compact, a laminate or a solid dispersion.

The use of the cello-oligosaccharide is not particularly restricted, but examples include food components, cosmetic components, dye components, flavor components, therapeutic components in medicines, pesticide components, feed components, fertilizer components, culture medium components, reagent components for analysis, additives, intermediate materials and fermentation materials in the fields of foods, cosmetics, medicines, general industrial products or the like.

Among foods, the cello-oligosaccharide produced by the method of the invention is used for example for gel such as jelly, pudding or yogurt; seasoning such as mayonnaise, dressing, sauce, baste, soup or processed vegetable products; retort-pouch foods and chilled foods such as curry, hashed beef, meat sauce, stew or soup; processed livestock products such as hamburger steak, bacon, sausage, salami sausage or ham; marine paste products such as steamed fish paste, hollow bamboo-shaped fish paste cake, fish meat ham/sausage or steamed and fried fish paste; processed wheat foods such as bread, uncooked noodle, dry noodle, macaroni, spaghetti, bread covering of Chinese filled bun, cake mix, premix, white sauce or skins of gyoza dumpling and spring roll; canned foods and bottled foods such as curry, sauce, soup, food boiled down in sweetened soy sauce or jam; snacks and confectionery such as candy, troche, tablet candy, chocolate, biscuit, cookies, rice crackers, Japanese- and Western-style sweets, cake with cream or fruit, snacks, sugar snacks or pudding; seasoned and processed foods such as deep-fried foods, croquette, gyoza dumpling or Chinese filled bun; pastes such as vegetable paste, minced meat, fruit paste or sea food paste; and the like.

In addition, the cello-oligosaccharide is used for example for dairy products such as ice cream, iced milk, ice cream with milk-solids content of 3% or more, whipped cream, condensed milk, butter, yogurt, cheese or white sauce; processed oils and fats such as margarine, fat spread or shortening; and the like. Moreover, the cello-oligosaccharide may be used for beverages including carbonated drink such as cola, fruit drink which is carbonated, contains alcohol or is mixed with a dairy product, fruit juice, or drink or lactic drink containing fruit; coffee; lactic acid/lactic drink such as milk, soymilk, chocolate milk, fruit milk or yogurt; tea drink such as green tea, oolong tea, powdered green tea or black tea; and the like.

The cello-oligosaccharide produced by the method of the invention is expected to have various physiological activities such as activation of intestinal useful flora, for example activation of lactic acid bacteria, lactobacilli and the like, lowering of blood sugar level and blood insulin level, lowering of blood cholesterol, lowering of body fat percentage, promotion of lipid/glucose metabolism, improvement of bowel movement/odor of feces and cariostatic effect. Thus, the cello-oligosaccharide may be used for functional foods, health foods, diet foods and the like as a physiologically active substance, in addition to the general food uses above.

Among general industrial products, the cello-oligosaccharide is used for example for food components, cosmetic components, dye components, flavor components, therapeutic components in medicines, pesticide components, feed components, fertilizer components, culture medium components, reagent components for analysis, additives, intermediate materials, fermentation materials and the like.

The cello-oligosaccharide produced by the method of the invention has a high purity and thus may be used as a material for chemical conversion into various cello-oligosaccharide derivatives.

The invention is explained more specifically based on the Examples and the like, but the invention is not limited by the Examples and the like.

Examples

[Production of Multiple Gene-Knockout Strains using Marker Recycling]
(1) Production of cbh2-Knockout Strain (ΔC2) and bgl1-Knockout Strain (ΔB1)

Figure 9:
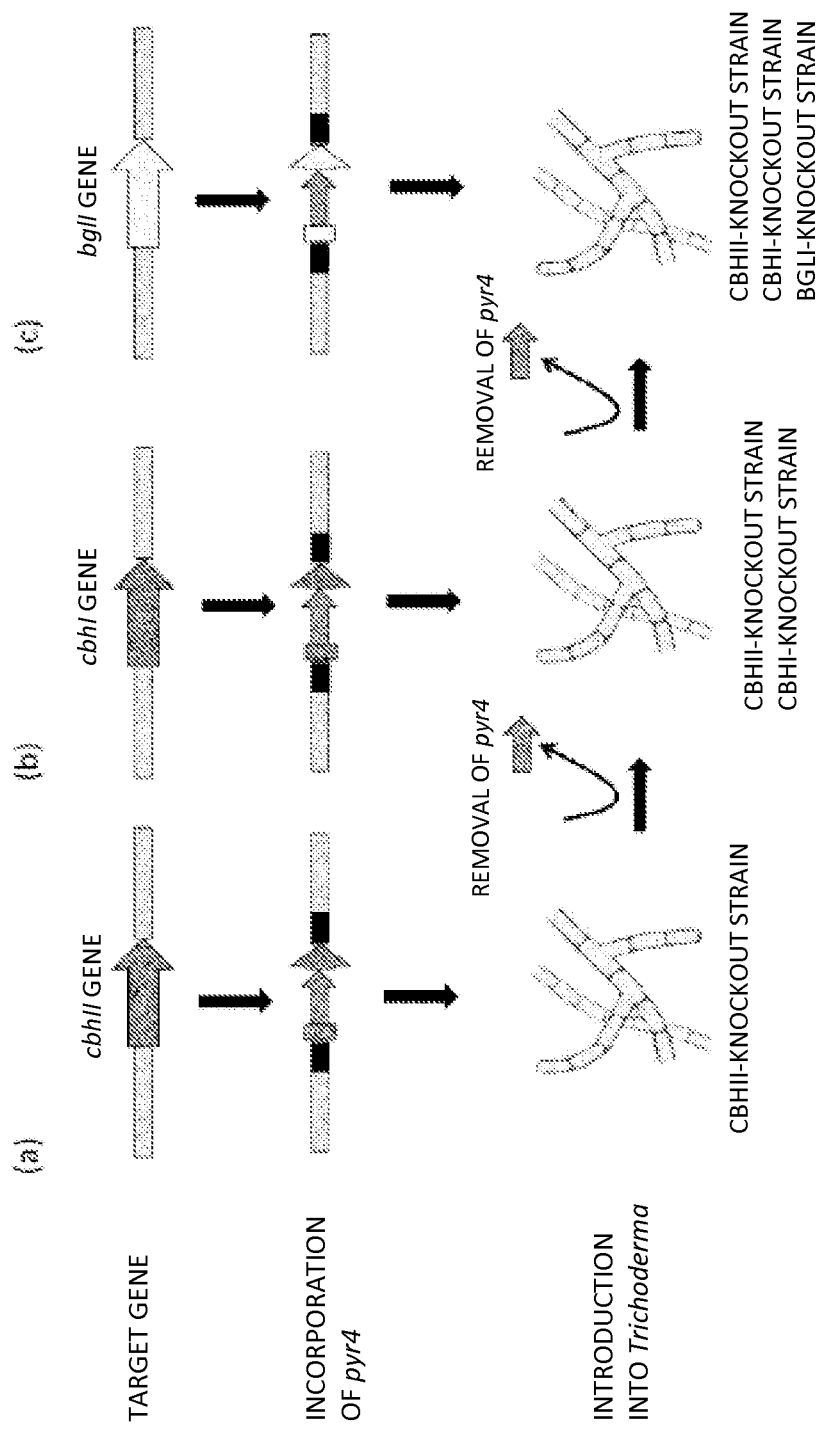
FIG. 9 shows schematic diagrams of a method for producing a multiple gene-knockout strain using marker recycling method.

As shown in FIG. 9 (a), a cbh2-knockout strain was obtained by marker recycling method. An uridine auxotrophic strain (pyr4$^-$) obtained through gene disruption using the resistance to 5-FOA as an index was transformed with a cbh2 gene disruption cassette by protoplast-PEG method, and transformants which grew in a culture medium containing no uridine were obtained. From the obtained transformants, strains each having one copy of the disruption cassette inserted at the target site through double crossover were selected by Southern blotting analysis. Then, spores of the obtained strains were applied on a culture medium containing 5-FOA, and colonies which regained the resistance to 5-FOA after pyr4 was removed through intramolecular homologous recombination and which grew on the culture medium were obtained. One of the strains was used as a cbh2-knockout strain (ΔC2). A bgl1-knockout strain (ΔB1) was produced by a similar method.
(2) Production of cbh1- and cbh2-knockout strain (~C2~C1), cbh1-, cbh2- and bgl1-knockout strain (ΔC2ΔC1ΔB1, triple enzyme gene-knockout strain) and cbh1-, cbh2-, bgl1- and egl1-knockout (ΔC2ΔC1ΔB1ΔEG1, quadruple enzyme gene-knockout strain)

Figure 10:
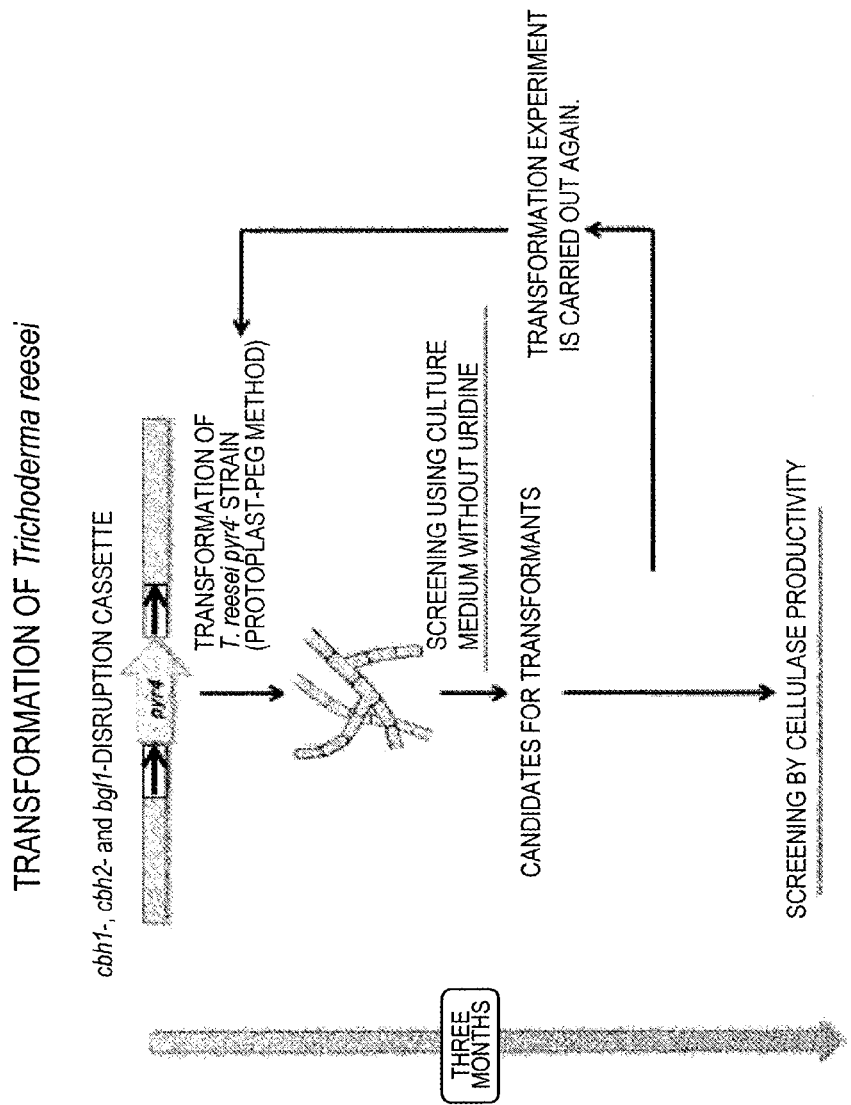
FIG. 10 shows a schematic diagram of transformation of *Trichoderma reesei*.

As shown in FIG. 9 (b), a cbh1- and cbh2-knockout strain was produced by marker recycling method using the cbh2-knockout strain. In addition, as shown in FIG. 9 (c) and FIG. 10, a cbh1-, cbh2- and bgl1-knockout strain was produced by marker recycling method using the cbh1- and cbh2-knockout strain. Moreover, a cbh1-, cbh2-, bgl1 and egl1-knockout strain was produced by marker recycling method using the cbh1-, cbh2- and bgl1-knockout strain.

[Evaluation of Gene-Knockout Strains]

In order to confirm the expression of cellulases of the obtained gene-knockout strains, $10^7$ spores were inoculated in a 300 mL Erlenmeyer flask containing 50 mL of a liquid culture medium for *Trichoderma reesei*. The composition of the culture medium was as follows.

1% Avicel, 0.14% $(NH_4)_2SO_4$, 0.2% $KH_2PO_4$, 0.03% $CaCl_2 \cdot 2H_2O$, 0.03% $MgSO_4 \cdot 7H_2O$, 0.1% Bacto Polypepton, 0.05% Bacto Yeast extract, 0.1% Tween 80, 0.1% trace element and 50 mM tartaric acid buffer (pH 4.0)

The composition of the trace element was as follows.

Figure 11:
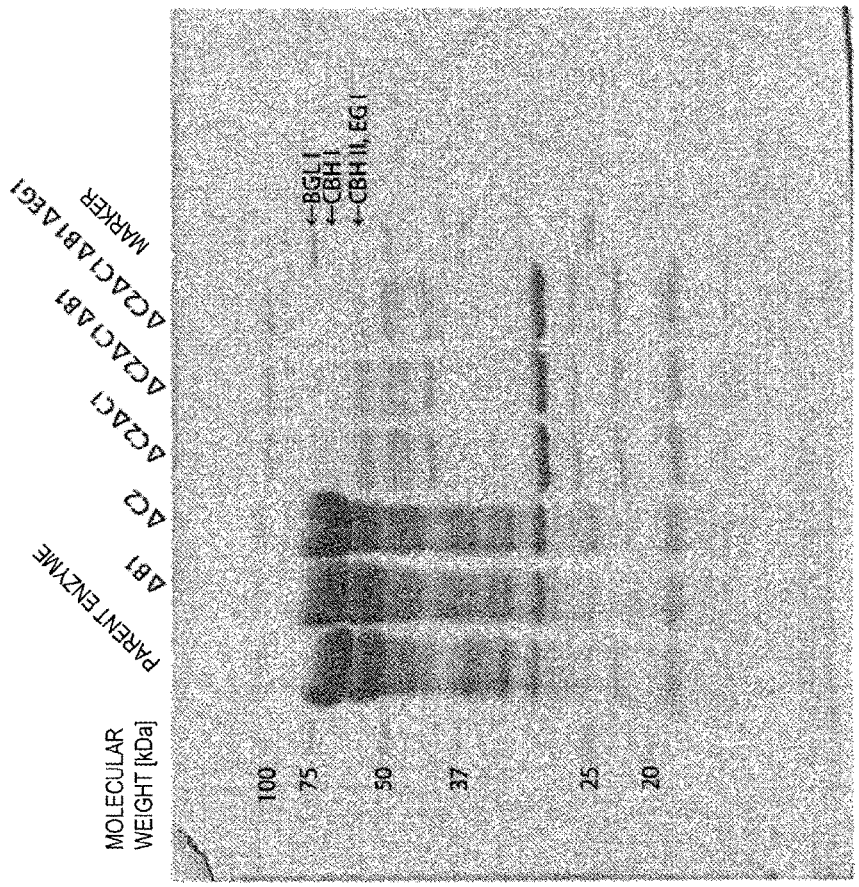
FIG. 11 shows the results of SDS-PAGE of the transformants produced in the Examples.

6 mg of $H_3BO_3$, 26 mg of $(NH_4)_6Mo_7O_{24} \cdot 4H_2O$, 100 mg of $FeCl_3 \cdot 6H_2O$, 40 mg of $CuSO_4 \cdot 5H_2O$, 8 mg of $MnCl_2 \cdot 4H_2O$ and 200 mg of $ZnCl_2$: the volume was adjusted to 100 ml by adding distilled water After cultivation at 220 rpm at 28° C. for seven days, the culture solutions were centrifuged at 3000 rpm for 15 minutes. The separated supernatants of the culture solutions were filtered through Sartolab (Sartorius Japan K.K.), and the obtained filtrates were used as the enzyme solutions. FIG. 11 shows the results of the SDS-PAGE of 20 μL of the obtained enzyme solutions.

Among the proteins secreted from *Trichoderma reesei*, the molecular weights of the cellulases encoded by the disrupted genes are 68 kDa (CBHI), 58 kDa (CBHII), 82 kDa (BGLI) and 54 kDa (EGI). As a result of the SDS-PAGE, the lack of the cellulase components encoded by the disrupted genes was confirmed.

Using the obtained enzyme solutions, (1) protein concentration, (2) β-glucosidase activity, (3) endoglucanase activity, (4) cellobiohydrolase activity, (5) cellobiase activity, (6) avicelase activity, (7) CMCase activity and (8) xylanase activity were measured by the following methods. The results are shown in FIG. 12 (a) to (d), FIG. 13 and FIG. 14.
(1) Protein Concentration Using Bio-Rad Protein Assay (Bio-Rad Laboratories, Inc.), the absorbance at 595 nm was measured, and the protein concentration was determined using bovine γ globulin as the standard substance.
(2) β-Glucosidase Activity Using cellobiose as the substrate, the glucose concentration was measured by Glucose CII Test Wako (Wako Pure Chemical Industries, Ltd.), and 1 U of β-glucosidase activity was defined as the amount of enzyme that hydrolyzed 1 μmol of cellobiose per minute.
(3) Endoglucanase Activity Using carboxymethylcellulose as the substrate, the resulting reducing sugar was measured by Somogyi-Nelson method, and 1 U of endoglucanase activity was defined as the amount of enzyme that released 1 μmol (in terms of glucose) of reducing sugar per minute.
(4) Cellobiohydrolase Activity Using crystalline cellulose as the substrate, the resulting reducing sugar was measured by Somogyi-Nelson method, and 1 U of cellobiohydrolase activity was defined as the amount of enzyme that released 1 μmol (in terms of glucose) of reducing sugar per minute.

(5) Cellobiase Activity

Using cellobiose as the substrate, the glucose concentration was measured by Glucose CII Test Wako (Wako Pure Chemical Industries, Ltd.), and 1 U of cellobiase activity was defined as the amount of enzyme that released 2 μmol of glucose per minute.

(6) Avicelase Activity

Using Avicel as the substrate, the resulting reducing sugar was measured by Somogyi-Nelson method, and 1 U of avicelase activity was defined as the amount of enzyme that released 1 μmol (in terms of glucose) of reducing sugar per minute.

(7) CMCase Activity

Using carboxymethylcellulose as the substrate, the resulting reducing sugar was measured by Somogyi-Nelson method, and 1 U of CMCase activity was defined as the amount of enzyme that released 1 μmol (in terms of glucose) of reducing sugar per minute.

(8) Xylanase Activity

Using xylan as the substrate, resulting xylose was measured using DNS (dinitrosalicylic acid) method, and 1 U of xylanase activity was defined as the amount of enzyme that released 1 μmol (in terms of xylose) of reducing sugar per minute.

[Production of Fractionated Enzymes by Enzyme Fractionation]

By eluting the fraction adsorbed onto DEAE-sepharose, which is an anion exchange resin, under the condition of 50 mM phosphate buffer (pH 6.0) with NaCl, CBH1 was removed from the cellulases obtained from the ΔC2 strain to obtain an enzyme sample. The enzyme sample was made pass through Mono-S, which is a cation exchange resin, under the condition of 50 mM acetic acid buffer (pH 4.0), and the fraction which was not adsorbed was used as the fractionated enzymes from which β-glucosidase 1 was removed (ΔC2-C1-B1).

[Evaluation of Oligosaccharide Productivity]

The oligosaccharide productivity of cellulases was evaluated using phosphoric acid-swollen cellulose as the substrate by HPLC analysis using KS-802, which is a column for sugar analysis.

(1) Evaluation of Oligosaccharide Productivity Using Enzymes Obtained from Single Gene-Knockout Strains The results of the evaluation of the oligosaccharide productivity of the cellulases obtained from the parent strain (*Trichoderma reesei* PC-3-7), the bgl1-knockout strain (ΔB1) and the cbh2-knockout strain (ΔC2) are shown in Table 2 and FIG. 15.

TABLE 2

| Sugar Recovery Rate [g-sugar/g-substrate] | | | |
|---|---|---|---|
| | PC-3-7 | ΔB1 | ΔC2 |
| G1 (Glucose) | 0.41 | 0.12 | 0.55 |
| G2 (Cellobiose) | 0.23 | 0.58 | 0.11 |

As shown in Table 2 and FIG. 15, through the oligosaccharide production using the cellulases obtained from the bgl1-knockout strain (ΔB1), cellobiose could be obtained in an amount 2.5 times as high as that of the parent strain.

(2) Evaluation of Oligosaccharide Productivity Using Enzymes Obtained from Triple Enzyme Gene-Knockout Strain The results of the evaluation of the oligosaccharide productivity of the cellulases obtained from the cbh1-, cbh2- and bgl1-knockout strain (ΔC2ΔC1ΔB1, a triple enzyme gene-knockout strain) are shown in Table 3 and FIG. 16.

TABLE 3

| Sugar Recover Rate [g-sugar/g-substrate] | | | | | | |
|---|---|---|---|---|---|---|
| Enzyme · Concentration · [g/L] | 0.01 | | 0.05 | | 0.10 | |
| Reaction · Period · [hr], | 24 | 48 | 24 | 48 | 24 | 48 |
| G1 · (Glucose) | 0.084 | 0.12 | 0.14 | 0.19 | 0.18 | 0.24 |
| G2 · (Cellobiose) | 0.19 | 0.22 | 0.23 | 0.24 | 0.23 | 0.23 |
| G3 · (Cellotriose) | 0.0063 | 0.0085 | 0.01 | 0.012 | 0.016 | 0.018 |
| G4 · (Cellotetraose) | — | — | — | — | 0.0033 | 0.0025 |

As shown in Table 3 and FIG. 16, it was found that the production amounts of cellotriose and cellotetraose as well as that of cellobiose increase through the oligosaccharide production using the cellulases obtained from the cbh1-, cbh2- and bgl1-knockout strain.

(3) Evaluation of Oligosaccharide Productivity Using Enzymes Obtained by Enzyme Fractionation and Enzymes Obtained from Triple Gene-Knockout Strain The oligosaccharide productivity was evaluated using the fractionated enzymes (ΔC2-C1-B1) prepared by removing CBH1, CBH2 and β-glucosidase 1 from the cellulases obtained from the parent strain (*Trichoderma reesei* PC3-7) and the cellulases obtained from the cbh1-, cbh2- and bgl1-knockout strain (ΔC2ΔC1ΔB1, a triple enzyme gene-knockout strain). The results are shown in Table 4 and FIG. 17.

TABLE 4

| Sugar Recovery Rate [g-sugar/g-substrate] | | |
|---|---|---|
| | ΔC2-C1-B1 | ΔC2ΔC1ΔB1 |
| G1 (Glucose) | 0.15 | 0.14 |
| G2 (Cellobiose) | 0.24 | 0.23 |

TABLE 4-continued

| Sugar Recovery Rate [g-sugar/g-substrate] | | |
|---|---|---|
| | ΔC2-C1-B1 | ΔC2ΔC1ΔB1 |
| G3 (Cellotriose) | 0.1 | 0.1 |
| G4 (Cellotetraose) | 0 | 0 |

As shown in Table 4 and FIG. 17, it was found that the cellulases obtained from the triple enzyme gene-knockout strain have oligosaccharide productivity comparable with that of the fractionated enzymes and have excellent productivity also with respect to cellotriose, which is a trisaccharide.

(4) Evaluation of Oligosaccharide Productivity Using Enzymes Obtained from Quadruple Enzyme Gene-Knockout Strain The results of the evaluation of the oligosaccharide productivity of the cellulases obtained from the cbh1-, cbh2-, bgl1- and egl1-knockout strain (ΔC2ΔC1ΔB1ΔEG1, a quadruple enzyme gene-knockout strain) are shown in Table 5 and FIG. 18.

enzyme gene-knockout strain) reached the maximum of 0.19 g/g-substrate when the saccharification period was 72 hours. When saccharification was carried out for 72 hours or longer, the production amount of the trisaccharide hardly changed, but the production amounts of the disaccharide and monosaccharide increased. From the results, it was found that the speed of the trisaccharide production and the speed of the cellotriose decomposition are in equilibrium at the enzyme saccharification period of 72 hours.

While the invention has been described in detail and with reference to specific embodiments thereof, it will be apparent to one skill in the art that various changes and modifications can be made therein without departing from the sprit and scope thereof. This application is based on Japanese patent application No. 2013-053166 filed on Mar. 15, 2013, the entire contents of which are incorporated hereinto by reference. All references cited herein are incorporated in their entirety.

INDUSTRIAL APPLICABILITY

Cello-oligosaccharides are believed to have various physiological activities and are believed to be very useful as

| | Sugar Recovery Rate[g-sugar/g-substrate] | | | | | | | |
|---|---|---|---|---|---|---|---|---|
| Enzyme · Concentration · [g/L] | 0.01 | | | | 0.05 | | | |
| Reaction · Period · [hr], | 12 | 24 | 48 | 72 | 12 | 24 | 48 | 72 |
| G1 · (Glucose) | 0.016 | 0.027 | 0.044 | 0.052 | 0.052 | 0.078 | 0.11 | 0.15 |
| G2 · (Cellobiose) | 0.068 | 0.11 | 0.14 | 0.16 | 0.15 | 0.19 | 0.22 | 0.24 |
| G3 · (Cellotriose) | 0.098 | 0.14 | 0.18 | 0.19 | 0.18 | 0.18 | 0.16 | 0.15 |
| G4 · (Cellotetraose) | 0.004 | 0.002 | — | — | — | — | 0.003 | 0.003 |

| | | | | |
|---|---|---|---|---|
| Enzyme · Concentration · [g/L] | 0.1 | | | |
| Reaction · Period · [hr], | 12 | 24 | 48 | 72 |
| G1 · (Glucose) | 0.073 | 0.11 | 0.18 | 0.23 |
| G2 · (Cellobiose) | 0.17 | 0.22 | 0.25 | 0.27 |
| G3 · (Cellotriose) | 0.17 | 0.16 | 0.13 | 0.12 |
| G4 · (Cellotetraose) | 0.003 | 0.004 | 0.004 | 0.004 |

As shown in Table 5 and FIG. 18, it was found that the cellulases obtained from the quadruple enzyme gene-knockout strain have oligosaccharide productivity comparable with that of the fractionated enzymes and have excellent productivity also with respect to cellotriose, which is a trisaccharide. It was found that the disruption of egl1 gene has higher effect of producing a cello-oligosaccharide composed of three or more monosaccharide units.

(5) Oligosaccharide Productivity and Influence of Saccharification Period Using Enzymes obtained from Quadruple Enzyme Gene-Knockout Strain As shown in FIG. 19, the production amount of cellotriose by the cellulases obtained from the cbh1-, cbh2-, bgl1- and egl1-knockout strain (ΔC2ΔC1ΔB1ΔEG1, a quadruple materials for functional foods. However, due to the complexity of the production method and the high production cost, cello-oligosaccharides have not been applied to industrial uses, and cellobiose, which is a disaccharide, accounts for 90% or more of the products distributed as cello-oligosaccharides. Moreover, pure cello-oligosaccharides composed of three or more cello-saccharide units are difficult to obtain, and their physiological functions have hardly been analyzed. The mutant cellulase-producing microorganism of the invention can produce not only cellobiose but also an oligosaccharide composed of three or more monosaccharide units and thus is very useful from the industrial and academic viewpoints.

The invention claimed is:

1. A mutant of a cellulase-producing microorganism, wherein two cellobiohydrolase genes, an endoglucanase gene and a β-glucosidase gene are completely physically deleted in the mutant, wherein the cellobiohydrolase genes are cbh1 and cbh2, the endoglucanase gene is egl1, and the β-glucosidase gene is bgl1, wherein no more than two cellobiohydrolase genes, no more than one endoglucanase gene and no more than one β-glucosidase gene are deleted or inactivated in the mutant,
wherein the mutant maintains cellulase-producing activity,
wherein said cellulase produced by the mutant is capable of producing cellotriose from a cellulosic material,
wherein the mutant is a microorganism belonging to the genus *Trichoderma*, and
wherein the specific activity of carboxymethylcellulase (CMCASE) produced by the mutant is below the specific activity of CMCASE produced by the native parent microorganism when cultured under the same conditions.

2. The mutant according to claim 1, wherein the microorganism belonging to the genus *Trichoderma* is one selected from the group consisting of *Trichoderma reesei*, *Trichoderma viride*, *Trichoderma atroviride* and *Trichoderma longibrachiatum*.

3. A method for producing a cellulase comprising culturing the mutant according to claim 1 in a culture medium to produce the cellulase.

* * * * *

SEQUENCE LISTING

<160> NUMBER OF SEQ ID NOS: 9

<210> SEQ ID NO 1
<211> LENGTH: 1671
<212> TYPE: DNA
<213> ORGANISM: Trichoderma reesei

<400> SEQUENCE: 1

| | | |
|---|---|---|
| atgtatcgga agttggccgt catcacggcc ttcttggcca cagctcgtgc tcagtcggcc | 60 |
| tgcactctcc aatcggagac tcacccgcct ctgacatggc agaaatgctc gtctggtggc | 120 |
| acttgcactc aacagacagg ctccgtggtc atcgacgcca actggcgctg gactcacgct | 180 |
| acgaacagca gcacgaactg ctacgatggc aacacttgga gctcgaccct atgtcctgac | 240 |
| aacgagacct gcgcgaagaa ctgctgtctg acggtgccg cctacgcgtc cacgtacgga | 300 |
| gttaccacga gcggtaacag cctctccatt ggctttgtca cccagtctgc gcagaagaac | 360 |
| gttggcgctc gcctttacct tatggcgagc gacacgacct accaggaatt caccctgctt | 420 |
| ggcaacgagt tctctttcga tgttgatgtt tcgcagctgc cgtaagtgac ttaccatgaa | 480 |
| cccctgacgt atcttcttgt gggctcccag ctgactggcc aatttaaggt gcggcttgaa | 540 |
| cggagctctc tacttcgtgt ccatggacgc ggatggtggc gtgagcaagt atcccaccaa | 600 |
| caacgctggc gccaagtacg gcacggggta ctgtgacagc cagtgtcccc gcgatctgaa | 660 |
| gttcatcaat ggccaggcca acgttgaggg ctgggagccg tcatccaaca acgcaaacac | 720 |
| gggcattgga ggacacggaa gctgctgctc tgagatggat atctgggagg ccaactccat | 780 |
| ctccgaggct cttacccccc accttgcac gactgtcggc aggagatct gcgagggtga | 840 |
| tgggtgcggc ggaacttact ccgataacag atatggcggc acttgcgatc ccgatggctg | 900 |
| cgactggaac ccataccgcc tgggcaacac cagcttctac ggccctggct caagctttac | 960 |
| cctcgatacc accaagaaat tgaccgttgt cacccagttc gagacgtcgg gtgccatcaa | 1020 |
| ccgatactat gtccagaatg gcgtcacttt ccagcagccc aacgccgagc ttggtagtta | 1080 |
| ctctggcaac gagctcaacg atgattactg cacagctgag gagacagaat cggcggatc | 1140 |
| tctttctcag acaagggcgg cctgactcag ttcaagaagg ctacctctgg cggcatggtt | 1200 |
| ctggtcatga gtctgtggga tgatgtgagt ttgatggaca acatgcgcg ttgacaaaga | 1260 |
| gtcaagcagc tgactgagat gttacagtac tacgccaaca tgctgtggct ggactccacc | 1320 |
| tacccgacaa cgagacctc ctccacaccc ggtgccgtgc gcggaagctg ctccaccagc | 1380 |
| tccggtgtcc ctgctcaggt cgaatctcag tctcccaacg ccaaggtcac cttctccaac | 1440 |
| atcaagttcg gacccattgg cagcaccggc aaccctagcg gcggcaaccc tcccggcgga | 1500 |
| aaccgtggca ccaccaccac ccgccgccca gccactacca ctggaagctc tcccggacct | 1560 |
| acccagtctc actacggcca gtgcggcggt attggctaca gcggcccac ggtctgcgcc | 1620 |
| agcggcacaa cttgccaggt cctgaaccct tactactctc agtgcctgta a | 1671 |

<210> SEQ ID NO 2
<211> LENGTH: 1609
<212> TYPE: DNA
<213> ORGANISM: Trichoderma reesei

<400> SEQUENCE: 2

| | | |
|---|---|---|
| atgattgtcg gcattctcac cacgctggct acgctggcca cactcgcagc tagtgtgcct | 60 |
| ctagaggagc ggcaagcttg ctcaagcgtc tggtaattat gtgaaccctc tcaagagacc | 120 |
| caaatactga gatatgtcaa ggggccaatg tggtggccag aattggtcgg gtccgacttg | 180 |

```
ctgtgcttcc ggaagcacat gcgtctactc caacgactat tactcccagt gtcttcccgg      240
cgctgcaagc tcaagctcgt ccacgcgcgc cgcgtcgacg acttctcgag tatccccac       300 aacatcccgg tcgagctccg cgacgcctcc acctggttct actactacca gagtacctcc      360
agtcggatcg ggaaccgcta cgtattcagg caaccctttt gttggggtca ctccttgggc      420
caatgcatat tacgcctctg aagttagcag cctcgctatt cctagcttga ctggagccat      480
ggccactgct gcagcagctg tcgcaaaggt tccctctttt atgtggctgt aggtcctccc      540
ggaaccaagg caatctgtta ctgaaggctc atcattcact gcagagatac tcttgacaag      600 accccctctca tggagcaaac cttggccgac atccgcaccg ccaacaagaa tggcggtaac      660
tatgccggac agtttgtggt gtatgacttg ccggatcgcg attgcgctgc ccttgcctcg      720
aatggcgaat actctattgc cgatggtggc gtcgccaaat ataagaacta tatcgacacc      780
attcgtcaaa ttgtcgtgga atattccgat atccggaccc tcctggttat tggtgagttt      840
aaacacctgc ctcccccccc ccttcccttc ctttcccgcc ggcatcttgt cgttgtgcta      900
actattgttc cctcttccag agcctgactc tcttgccaac ctggtgacca acctcggtac      960
tccaaagtgt gccaatgctc agtcagccta ccttgagtgc atcaactacg ccgtcacaca     1020
gctgaacctt ccaaatgttg cgatgtattt ggacgctggc catgcaggat ggcttggctg     1080
gccggcaaac caagacccgg ccgctcagct atttgcaaat gtttacaaga atgcatcgtc     1140
tccgagagct cttcgcggat tggcaaccaa tgtcgccaac tacaacgggt ggaacattac     1200 cagccccca tcgtacacgc aaggcaacgc tgtctacaac gagaagctgt acatccacgc     1260 tattggaccct cttcttgcca atcacggctg gtccaacgcc ttcttcatca ctgatcaagg     1320
tcgatcggga aagcagccta ccggacagca acagtgggga gactggtgca atgtgatcgg     1380
caccggattt ggtattcgcc catccgcaaa cactggggac tcgttgctgg attcgtttgt     1440
ctgggtcaag ccaggcggcg agtgtgacgg caccagcgac agcagtgcgc cacgatttga     1500
ctcccactgt gcgctcccag atgccttgca accggcgcct caagctggtg cttggttcca     1560
agcctacttt gtgcagcttc tcacaaacgc aaacccatcg ttcctgtaa                 1609
```

<210> SEQ ID NO 3
<211> LENGTH: 2368
<212> TYPE: DNA
<213> ORGANISM: Trichoderma reesei

<400> SEQUENCE: 3

```
atgcgttacc gaacagcagc tgcgctggca cttgccactg ggccctttgc tagggcagac       60
agtcagtata gctggtccat actgggatgt atatgtatcc tggagacacc atgctgactc      120
ttgaatcaag gtagctcaac atcggggccc tcggctgagg cagttgtacc tcctgcaggg      180
actccatggg gaaccgcgta cgacaaggcg aaggccgcat tggcaaagct caatctccaa      240
gataaggtcg gcatcgtgag cggtgtcggc tggaacggcg tccttgcgt tggaaacaca      300 tctccggcct ccaagatcag ctatccatcg ctatgccttc aagacggacc cctcggtgtt      360
cgatactcga caggcagcac agcctttacg ccgggcgttc aagcggcctc gacgtgggat      420
gtcaatttga tccgcgaacg tggacagttc atcggtgagg aggtgaaggc ctcggggatt      480
catgtcatac ttggtcctgt ggctgggccg ctgggaaaga ctccgcaggg cggtcgcaac      540
tgggagggct tcggtgtcga tccatatctc acgggcattg ccatgggtca aaccatcaac      600
ggcatccagt cggtaggcgt gcaggcgaca gcgaagcact atatcctcaa cgagcaggag      660
```

```
ctcaatcgag aaaccatttc gagcaaccca gatgaccgaa ctctccatga gctgtatact    720
tggccatttg ccgacgcggt tcaggccaat gtcgcttctg tcatgtgctc gtacaacaag    780
gtcaatacca cctgggcctg cgaggatcag tacacgctgc agactgtgct gaaagaccag    840
ctggggttcc caggctatgt catgacggac tggaacgcac agcacacgac tgtccaaagc    900
gcgaattctg ggcttgacat gtcaatgcct ggcacagact tcaacggtaa caatcggctc    960
tggggtccag ctctcaccaa tgcggtaaat agcaatcagg tccccacgag cagagtcgac   1020
gatatggtga ctcgtatcct cgccgcatgg tacttgacag gccaggacca ggcaggctat   1080
ccgtcgttca acatcagcag aaatgttcaa ggaaaccaca agaccaatgt cagggcaatt   1140
gccagggacg gcatcgttct gctcaagaat gacgccaaca tcctgccgct caagaagccc   1200
gctagcattg ccgtcgttgg atctgccgca atcattggta accacgccag aaactcgccc   1260
tcgtgcaacg acaaaggctg cgacgacggg gccttgggca tgggttgggg ttccggcgcc   1320
gtcaactatc cgtacttcgt cgcgccctac gatgccatca ataccagagc gtcttcgcag   1380
ggcacccagg ttaccttgag caacaccgac aacacgtcct caggcgcatc tgcagcaaga   1440
ggaaaggacg tcgccatcgt cttcatcacc gccgactcgg gtgaaggcta catcaccgtg   1500
gagggcaacg cgggcgatcg caacaacctg gatccgtggc acaacggcaa tgccctggtc   1560
caggcggtgg ccggtgccaa cagcaacgtc attgttgttg tccactccgt tggcgccatc   1620
attctggagc agattcttgc tcttccgcag gtcaaggccg ttgtctgggc gggtcttcct   1680
tctcaggaga gcggcaatgc gctcgtcgac gtgctgtggg gagatgtcag cccttctggc   1740
aagctggtgt acaccattgc gaagagcccc aatgactata acactcgcat cgtttccggc   1800
ggcagtgaca gcttcagcga gggactgttc atcgactata agcacttcga cgacgccaat   1860
atcacgccgc ggtacgagtt cggctatgga ctgtgtaagt ttgctaacct gaacaatcta   1920
ttagacaggt tgactgacgg atgactgtgg aatgatagct tacaccaagt tcaactactc   1980
acgcctctcc gtcttgtcga ccgccaagtc tggtcctgcg actggggccg ttgtgccggg   2040
aggcccgagt gatctgttcc agaatgtcgc gacagtcacc gttgacatcg caaactctgg   2100
ccaagtgact ggtgccgagg tagcccagct gtacatcacc tacccatctt cagcacccag   2160
gaccctccg aagcagctgc gaggctttgc caagctgaac ctcacgcctg tcagagcgg    2220
aacagcaacg ttcaacatcc gacgacgaga tctcagctac tgggacacgg cttcgcagaa   2280
atgggtggtg ccgtcggggt cgtttggcat cagcgtggga gcgagcagcc gggatatcag   2340
gctgacgagc actctgtcgg tagcgtag                                      2368
```

<210> SEQ ID NO 4
<211> LENGTH: 3194
<212> TYPE: DNA
<213> ORGANISM: Trichoderma reesei

<400> SEQUENCE: 4

```
atgaagacgt tgtcagtgtt tgctgccgcc cttttggcgg ccgtagctga ggccaatgta    60
cgttcccttc tgccctgttg taactgcacc caagacattg ccctctcccc cttttgcct   120
tgaacaactg cagcttttcc tccttgctgg atcatcggac gcctgcagaa ttatcagccc   180
cattggcttt ctgtgtcaat gcacttgcaa gagcctgtcg attcgcgagt ctcctgattc   240
acagccccta ttccctagcg aagctctgcc ctgatcgact tcccactttc cctccatgca   300
gaaatcggta cagttgagcc agggaaagcg gtttggacaa cattggcagg cagtcttgc    360
attgggtcgc ttccgccagg tttactgctg ctgttatatc ttgtcgtgac atcccggtgc   420
```

```
tttacttccc cttctcccct cacctcacag ccttccacgg cgtacccagc catcaccgt      480 tttcgctatg aaggcatcat ttcttttggc tgcctccacg gcgacaattt tggatcttgt      540
gacagctgct gacactcgtt tgaacgcaca gccctacccg cctcctcact ccaaccaggc      600
gtactcgcct cctttctacc cttcgccatg gatggacccc agtgctccag ctgggagca      660 agcctatgcc caagctaagg agttcgtctc gggcttgact ctcttggaga aggtcaacct      720
caccaccggt gttgggtaag ctctttatat ggatcacgtc tgcagtcaag cgtgctaatc      780
attcttgtag ctggatgggt gagaagtgcg ttggaaacgt tggtaccgtg cctcgcttgg      840
gcatgcgaag tctttgcatg caggacggcc ccctgggtct ccgattcaac acgtacaaca      900
gcgctttcag cgttggcttg acggccgccg ccagctggag ccgacaccttt ggggttgacc      960 gcggtaccgc tctgggctcc gaggcaaagg caagggtgt cgatgttctt ctcggacccg     1020
tggctggccc tctcggtcgc aaccccaacg gaggccgtaa cgtcgagggt ttcggctcgg     1080
atccctatct ggcgggtttg gctctggccg ataccgtgac cggaatccag aacgcgggca     1140
ccatcgcctg tgccaagcac ttcctcctca acgagcagga gcatttccgc caggtcggcg     1200
aagctaacgg ctacggatac cccatcaccg aggctctgtc ttccaacgtt gatgacaaga     1260
cgattcacga ggtgtacggc tggcccttcc aggatgctgt caaggctggt gtcgggtcca     1320
tcatgtgctc gtacaaccag gtcaacaact cgtacgcttg ccaaaactcc aagctcatca     1380
acggcttgct caaggaggag tacggttcc aaggctttgt catgagcgac tggcaggccc     1440
agcacacggg tgtcgcgtct gctgttgccg gtctcgatat gaccatgcct ggtgacaccg     1500
ccttcaacac cggcgcatcc tactttggaa gcaacctgac gcttgctgtt ctcaacggca     1560
ccgtccccga gtggcgcatt gacgacatgg tgatgcgtat catggctccc ttcttcaagg     1620
tgggcaagac ggttgacagc ctcattgaca ccaactttga ttcttggacc aatggcgagt     1680
acggctacgt tcaggccgcc gtcaatgaga actgggagaa ggtcaactac ggcgtcgatg     1740
tccgcgccaa ccatgcgaac cacatccgcg aggttggcgc caagggaact gtcatcttca     1800
agaacaacgg catcctgccc cttaagaagc ccaagttcct gaccgtcatt ggtgaggatg     1860
ctggcggcaa ccctgccggc cccaacggct gcggtgaccg cggctgtgac gacggcactc     1920
ttgccatgga gtggggatct ggtactacca acttcccta cctcgtcacc ccgacgcgg      1980 ccctgcagag ccaggctctc caggacggca cccgctacga gagcatcctg tccaactacg     2040
ccatctcgca gacccaggcg ctcgtcagcc agcccgatgc cattgccatt gtctttgcca     2100
actcggatag cggcgagggc tacatcaacg tcgatggcaa cgagggcgac cgcaagaacc     2160
tgacgctgtg gaagaacggc gacgatctga tcaagactgt tgctgctgtc aaccccaaga     2220
cgattgtcgt catccactcg accggccccg tgattctcaa ggactacgcc aaccaccca      2280 acatctctgc cattctgtgg gccggtgctc ctggccagga gtctggcaac tcgctggtcg     2340
acattctgta cggcaagcag agcccggccc gcactccctt cacctgggc ccgtcgctgg     2400 agagctacgg agttagtgtt atgaccacgc ccaacaacgg caacggcgct ccccaggata     2460
acttcaacga gggcgccttc atcgactacc gctactttga caaggtggct cccggcaagc     2520
ctcgcagctc ggacaaggct cccacgtacg agtttggctt cggactgtcg tggtcgacgt     2580
tcaagttctc caacctccac atccagaaga caatgtcgg ccccatgagc ccgcccaacg     2640
gcaagacgat tgcggctccc tctctgggca gcttcagcaa gaaccttaag gactatggct     2700
tccccaagaa cgttcgccgc atcaaggagt ttatctaccc ctacctgagc accactacct     2760
```

-continued

| | |
|---|---|
| ctggcaagga ggcgtcgggt gacgctcact acggccagac tgcgaaggag ttcctccccg | 2820 |
| ccggtgccct ggacggcagc cctcagcctc gctctgcggc ctctggcgaa cccggcggca | 2880 |
| accgccagct gtacgacatt ctctacaccg tgacggccac cattaccaac acgggctcgg | 2940 |
| tcatggacga cgccgttccc cagctgtacc tgagccacgg cggtcccaac gagccgccca | 3000 |
| aggtgctgcg tggcttcgac cgcatcgagc gcattgctcc cggccagagc gtcacgttca | 3060 |
| aggcagacct gacgcgccgt gacctgtcca actgggacac gaagaagcag cagtgggtca | 3120 |
| ttaccgacta ccccaagact gtgtacgtgg gcagctcctc gcgcgacctg ccgctgagcg | 3180 |
| cccgcctgcc atga | 3194 |

<210> SEQ ID NO 5
<211> LENGTH: 2625
<212> TYPE: DNA
<213> ORGANISM: Trichoderma reesei

<400> SEQUENCE: 5

| | |
|---|---|
| atgcggctgt gtgacttatc cagccttgcg agctgggtcc tcgtgacagt agctctgcct | 60 |
| tcgagcggcg ctgctgccaa aggcgtctcg caaataccct caacacgtat gtactcagct | 120 |
| aatcttctgg tatatgggac gtgtttcatg ctgtgtgatc aacactaaga cacatctgta | 180 |
| gattcaagtc aaagcaaagg aaatggaccg tgggctcacg cgtatcgtcg cgccgagaag | 240 |
| ttagtgcgac aaatgacact cgaagaaaag gccaacatca cgcgcggatt caccggcgac | 300 |
| aatgtctgtg ccggcaacac tggctctgtt cctcgcctgg gatggcccgg catgtgtgtc | 360 |
| cacgatgccg gcaacggagt tcgcgcaacc gacttggtca attcttatcc ctctggcatc | 420 |
| cacgtcgggg cgagctggga tcgaaacctg acgtacgaga gggggcttca tatgggcggg | 480 |
| gagttcaaag caaaggagg taagaatttc tgtttctctc cgtccttctt cagtatcaat | 540 |
| tctttgctta tgggcaccgt cagtcaacgt cccactcggt cccaatgctg gccgctagg | 600 |
| gcgaacacct ctgggtggtc gaaactggga gggtttctcc atcgatccgt atctctctgg | 660 |
| ccaattgaac gcagagacaa tcactggaat gcaagatgcc ggagtgattg cgaacatcaa | 720 |
| ggtactatcc ggtgatttgg aaggagcatg ttgtgtgtgt aaattactat actgatctgt | 780 |
| tgaccccgta gcatttcatc gccaacgaac aagagacgct tcggcgtccc tactttggtg | 840 |
| tcgaagctgt ttctgcaaat atcgatgaca gaaccctaca cgaatactat ctctggccct | 900 |
| ttatggatag tgtgcatgct ggcgtgggat ccgtcatgtg ctcctataac aggatcaaca | 960 |
| acacgtacgg atgcatgaac acaagcttat gaacggaat tctcaaggct gaattgggct | 1020 |
| ttcaaggttt cgtcatgctt gactggaatg ctcagcacga tctgcaaagc gccaatgccg | 1080 |
| gactcgacat ggtgatgccc ctcggtggtt cttggggcaa gaatctgaca gatgctgttg | 1140 |
| caaacgggac ggtcagcgag tctcggatta cggacatggc cacgaggtaa gatgcctgac | 1200 |
| cgcactgtcg atacatgagt tcgtgcttac tttgcttcgc aaaggatcat gctgcatgg | 1260 |
| tacttagtcg gtcaagatgg caacaacttt ccagtaccgg gcatcggctt gaaacagctc | 1320 |
| acgaaaccgc acgagcaagt cgacgcacgc gatcccgcat cgaagcccgt gcttctggag | 1380 |
| ggcgccattg caggacacgt tctagtcaag aacgaaaaca atgcgctacc gttcaacaag | 1440 |
| aagctaacca tgatctccgt ctttggctac gatgctacga tcccacgcac aaagaatacc | 1500 |
| gacattcttt tccagctcgg atataccctct tcgccggaga tggctcaggc cgtacttggc | 1560 |
| aatgaggcgc atttcgacca ggcagcaaag ggagggacaa ttatgactgg cgggcgagct | 1620 |
| ggcgcaaacg ctccatcata catcgacgat gtacacggct cttcttcccc tatttgctgt | 1680 |

-continued

```
agaatttttt ttgactgacg attgatctag ccgcttgctg ctatccaacg tcgagcccgc   1740
aaagatgata cttgggtaaa ttgggacctg gactccttca atccggaagt caatgctgct   1800
tcagatgctt gcttggtctt catcaatgcc atcgcaacag agggctggga ccgtgacggc   1860
ctccatgacg attttagtga cggccttgtc ttgaatgtag ccgccaactg ctccaacacg   1920
attgtcgtcg ttcacgccgc gggcactcgc ctggttgacc aatggattga gcatcccaat   1980
gttactgccg ccgtcatcgc gcatcttcca ggccaggaca cgggtagagc cctcgtgaag   2040
cttctttatg gcgaagccaa cttctctggc aaacttccct atacaattgc caagaacgag   2100
agcgattact cagtttacac cccatgccag cgacgctctc ccgaagacac cgatcccag    2160
tgcgatttca ccgaaggcgt ctatctcgat tatcgcgctt ttgatgcgaa caacatgact   2220
ccccgcttcg agttcggata cgggctcagc tacacgtcgt tcaattactc agctctctcc   2280
atcaaaaagg caagggcct tcggcagtca aggtgtaccg acgatctttg gcaagccgct    2340
gcacaagtca ccgcaagcat caccaacagt ggcggcatgt ctggaagtga ggttgcgcag   2400
ctgtacttgg ccattccaaa tagcccgcca agcaattgc gcggattcaa caaactgttg     2460
ctgcgtccac atgagtctgg aactgttcac tttggactca cgaagcgaga cttaagtgtt   2520
tgggatgttg tttctcagtc gtgggttatt caggagggtg agtacaaggt atttgttggg   2580
gcgagcagcc gcgatattcg actcagtgga aaactgcata tttag                   2625
```

<210> SEQ ID NO 6
<211> LENGTH: 2807
<212> TYPE: DNA
<213> ORGANISM: Trichoderma reesei

<400> SEQUENCE: 6

```
atgactctgg cagaaaagac caatatcact gcaggaactg gcatctatat gggtgagtgg     60
tggcttcctt gaggatgaga ggcagtttca gactgtgtgt ggatgagcga gtaattgtat    120
gctaaccagc gagaacaggg tgagttattt ggagccttgc caacgtacag accgaagcct   180
cttcaaggga tgaaaggctt ttgtcagaac ttcagcaaac gggtcttgta caccatatgc   240
tgggatgatg ataacccatt gagagattat aaactaacac tgatcaaggc gatgtgccgg   300
aaacacaggc tctgcgtttc gagtttcctt tccccagctg tgtctcaacg acagcccggc   360
gggtgtccga catgcggaca atgtaacagc ttttcctgac ggaatcaccg tcggcgcaac   420
gttcgacaag gccctcatgt acaagcgcgg cgtggccatt ggaaaggaga ccgcggaaa     480
gggcgtcaat gtctggctgg gaccaactgt gggccgata ggccgcaagc caagggcgg     540
ccgcaactgg gaaggcttcg gtgctgatcc tgtgctccag gccgtcggtg ctcgagagac   600
gatcaagggc gttcaagagc aggggtcat tgcgactatc aaacacttta tcggcaacga    660
gcaggagatg taccgcatgt acaatcccct tcaatacgca tacagctcaa atattggtac   720
gtgttttccag cggaatgaag agtaaaagtg agataagatg ctgacaatga gttgacgggt  780
aaaagacgat aggacgctgc atgaagtata tgcctggcca ttcgccgagg gcatccgagc   840
gggtgttggc gccgtcatga tggcttacaa tgctgtaagt gattctgaga cgagtggctt   900
gattgtccag cagctaattg cttttctccc gccaggtgaa cgggactgcg tgctctcaac   960
acccatatct tatgagtgcc cttctcaagg atgagatggg cttcaaggc ttcatcatga    1020
ccgactggct cgctcacatg tctggcgtcg cttctgccat tgccggcctg atatggaca    1080
tgcctggcga cgttcagatt cccttcttcg gcggctcata ctggatgtat gagctcactc   1140
```

-continued

| | |
|---|---:|
| ggtctgctct taatggttcg gttcccatgg atcgcatcaa cgacgcggct acacgcatag | 1200 |
| ccgctgcgtg gtacaagatg ggccaggaca agggattccc cgcgacgaat tcgacacca | 1260 |
| actctcgtgc tgccttcaac ccgctgtatc ctgccgcgct gccactttcg ccatttggca | 1320 |
| tcacaaacga gtttgtaccg gtccaagacg atcacgacg aattgctcgc caaatttctc | 1380 |
| aggaagcaat cacccctgttg aagaacgacg gcgacatcct ccctctatcg ccttcgcagc | 1440 |
| acctcaaggt tttcggcacc gatgctcaga aaaacccaga cggcatcaat tcatgcacag | 1500 |
| atcgcaattg caacaaggga actctgggcc aaggatgggg ctcgggaact gtcgattacc | 1560 |
| cctatttgga cgatcccatc tcagctatca ctgcagaggc cgacaatgtc acgttttaca | 1620 |
| acacggacaa gttcccttct gtcggcgaag tatcagatag cgacgtcgcc atcgtctttg | 1680 |
| tcaactcgga tgctggcgaa acacctaca ccgtggaagg caaccacggc gaccgtgaca | 1740 |
| aatccggctt gtacgcatgg cacgacggcg ataagcttgt gcaggacgcc gcgagcaagt | 1800 |
| tcagcaacgt cattgtcgtg atacacactg ttggcccccct gatcctcgag aagtggatcg | 1860 |
| atctgccatc cgtcaaggcg gtgctcgtcg cacatctgcc cggccaggaa gccggcaagt | 1920 |
| ctcttacaaa cgtcctcttt ggacacgcct cgccgtgcgg acacttgcct tattccatca | 1980 |
| cgaaagagga ggacgacctt cccaaaagcg tcactacgct cattgactcg gagttcctca | 2040 |
| accagcccca agacacatac acagagggtc tgtacattga ctaccgctgg ctcaacaaga | 2100 |
| acaagaccaa gcctcgctac gcctttggcc acggtctgag ctacacaaac ttcaccttca | 2160 |
| aggcagcatc catcaaacag gtcgccaggc tgagcgcata cccgccggct cgcccagcca | 2220 |
| agggcagcac ccccgatttt gcgcaatcca ttccatccgc aagcgaagcc gttgcgccgt | 2280 |
| caggcttcgg caagatcccc cgctacatct actcttggct gtcgcagggc gatgccaacc | 2340 |
| gggccatttc agacggcaag acgggcaagt atccgtatcc cgacggctac tctaccaccc | 2400 |
| agaagcccgg cgctcgcgct ggcggcggcg agggaggcaa ccccgcgctc tgggacgttg | 2460 |
| cgtacagcct cacggtgacg gtgcagaata cgggcgatga gtatgctggc aaggcctccg | 2520 |
| tgcaggcata tctccaattc ccggacgata tcgactacga tacgccaatc attcagctcc | 2580 |
| gtgactttga aaagacaaag gagctaaagc cgggggagac gacgactgtg acgctgactc | 2640 |
| ttacacgcaa ggacgtcagt gtgtgggacg tggtggcgca ggattggaag gttcctgcgg | 2700 |
| ttgacggagg gtataaggtg tggattgggg atgccagtga ttcgttaagt attgtatgtc | 2760 |
| atacggatac gttggagtgt gagactggtg ttgttgggcc tgtgtag | 2807 |

<210> SEQ ID NO 7
<211> LENGTH: 2808
<212> TYPE: DNA
<213> ORGANISM: Trichoderma reesei

<400> SEQUENCE: 7

| | |
|---|---:|
| atggtagctg tcaagcagat tgccctgctt gcgggccttg cccactgggc agatgccgca | 60 |
| gaaaaggtca tcaccaacga cactcacttc tacgccaat cgccccctgt ttatccatca | 120 |
| cgtatgctct accggtttct cttcaatgaa atgggaagac catgatactg atggcgtcaa | 180 |
| cgactagctg aaatgactgg tggcaacgaa tgggaggcgc gtatcaaaa ggccaaagcc | 240 |
| tttgtcggcc agttgactct agaggaaaag gtgagcaacg acgacggcca cacaaagaca | 300 |
| cgtgcaatcg acaaagcagg gctggctcgt ctaacgttca tcaggtcaat ctcaccgctg | 360 |
| gggtcccgcc caatactacc tgcagcggcg tgattcccgc catcgagcgt ctcaagttcc | 420 |
| ccggcatgtg cctcagcgat gctggcaatg gccttcgcaa cacggatttt gtcagtggct | 480 |

```
tccccagtgg aatccatgtg ggtgccaggt gagtgaccga gtcggtttac ttgagttgaa    540
catgtgcccc caaaccoccc ctcaagctac agtatcaagc taaccgcgcc cagctggagc    600
aaggacttgg ctttccgacg cgccgttgcc atgggtgccg agttcagaaa gaagggtgtc    660
aatgtcttgc tcgggcccgt ggttggccct gctgggcgta ccgtacgtgg agggagaaac    720
tgggaaggct tctccgttga cccctggctg gcaggagtct tggtctccga ccgtttcct    780
ggcatccagg aacagggcgt tatcacgagt accaaagtag gtcgtctcct aattgtaaca    840
accgactgtc ccccgaaagt tggctactga taaccatgcg tgtagcatta cattctcaac    900
gagcaggaga ctcatcgcat gccagaagcg aacgtctctg ctgtttcttc aaatattgac    960
gacaagacga tgcatgagta ttacttatgg taagtataga ccgcttctct tctgcctttg    1020
caatgaagtt ctgatgactt cactaggcct tttcaagacg ctgtgagagc gggcagcgga    1080
aacatcatgt gctcttacca gcgtatcaac aactcgtacg gctgttccaa cagcaagact    1140
ctgaatggcc ttctgaagac tgagcttggc tttcaggtgt gcagccactc ccttcatgtc    1200
tctactcaat ggcactgacc caaagttttg aattaagggg tttgtcgttt ccgactggtc    1260
tgctcagcat gctggagtgg cttctgcaga agctggcatg gatatggcca tgcctgggcc    1320
ggccgagttc tggggcgagc atctggttga ggctgtgaaa aatggttcat tgcccgagtc    1380
acgaataacg gatatggcaa cgaggtaaag acaatgagag ttatcaagaa ttgcatatac    1440
taacgcgcct acaggatcat cgccacttgg tatcagttcg accaggacaa cggcattcca    1500
aagccgggaa tcgggatgcc gtccaacgtt ctggattctc atgaaattgt tgatgcgcga    1560
gatcctgctg ctgtaccggt ccttctcaat ggcgccattg aaggtcatgt cctcgtcaag    1620
aacaccaaga acacgctacc cctgaagaag ccgcggaagc tctctctctt cggctattca    1680
gccacaactc ccgacttctt cagtccatcc agggatgagc aactcagcga cagctggatc    1740
ttcggtaagg aggcgtacaa ttccaactac ctctcaccgg acggtttcgc cacgtttggt    1800
agaaatggta ctacgtttgg cggctgtggc tctggcgcca tcacacccgc actggcaatc    1860
tctccttttcg aggctctgaa gtggagggct gcccaagatg gaacagcaac attcaacaac    1920
tttttatccg acaagccgga tgttgatcca acctctgacg cctgcatcgt gtttggcaac    1980
gcatacgcct gtgaaggaaa cgaccggccg gctatccaag acgactacac agacgaccta    2040
atcaaagcag tggccagcca gtgcaacaag accattgttg tcctccacaa cgcaggaatt    2100
cggctggtcg acggctttgt tgaccatcca aacatcacag cagtcatctt tgcacatttg    2160
ccgggtcagg agagcggacc agcgcttacc tcacttctct atggggagac cagcccctct    2220
ggtaggctgc cgtacaccgt tgcaaagaac gataccgatt atggcgtcgt tctcgatccg    2280
gcacaggcga cgggcgagtt tgcctacttt ccacaggccg acttcaagga aggcgtctat    2340
ctcgactatc gttactttga taaggagggc attgaaccac gctatgagtt tggctttgga    2400
ctgagctaca caacctttgc gtaccttaac ctgtctgtcg accatgtttc aggggcaaac    2460
acgtatccat ggccgggagg ccctattgtc agcggtgggc aaacggacct ctgggatgct    2520
attgctaccg tcagcgttga tattcgcaac acgggcagtg ttgcaagcta cgaagtggca    2580
cagctctaca ttggcattcc ggggctccg gcgaagcaac tccgtgggtt cgagaagccc    2640
tttttgcggc ccaacgagtc gcagtcggtg acgttccatc tcacaaggag agacttgagc    2700
gtttggagcg tagagaggca gaagtggcag ctgcagcagg gcatacacaa gatttacgtt    2760
ggcagcagca gcagacgact gcatgtcaat gggacgctgg acatctga             2808
```

<210> SEQ ID NO 8
<211> LENGTH: 1831
<212> TYPE: DNA
<213> ORGANISM: Trichoderma reesei

<400> SEQUENCE: 8

| | | | | | |
|---|---|---|---|---|---|
| gtcgacaact | gcatccaaac | catcctacca | aatgaaaaat | gcccgagggt | gatatgttcc | 60 |
| ctccacgcgc | aaaagcaaat | gccaaatcaa | aaatacaatt | ccatgcttcc | agatccacca | 120 |
| gatatgtcag | gaccatatat | gaaccttcca | atgtgcagtt | cgcctccgcc | atcgcgtgtt | 180 |
| gttgcatgca | aagatacaca | tcaatcgcag | ctggggtaca | atcatccatc | atcccaactg | 240 |
| gtacgtcata | acaaaaatcg | acaagatgga | aaaagaggtc | gcctaaatac | agctgcattc | 300 |
| tatgatgccg | ggcttttggac | aagagctctt | tctcagctcc | gtttgtcctc | cctcccttt | 360 |
| cccccttctt | gctaaatgcc | tttctttact | tctttcttcc | cttccctccc | ctatcgcagc | 420 |
| agcctctcgg | tgtaggcttt | ccacgctgct | gatcggtacc | gctctgcctc | ctctacgggg | 480 |
| tctgaggcct | tgaggatgcc | ccggcccaca | atggcaatgt | cgctgccggc | gatgccaatc | 540 |
| agcttgtgcg | gcgtgttgta | ctgctggccc | tggccgtctc | caccgaccga | tccgttggtc | 600 |
| tgctggtcct | cgtcttcggg | gggcagctgg | cagccgggcg | tcatgtggat | aaaggcatcg | 660 |
| tcgggctcgg | tgttgagcgt | ctcctgcgag | atgaagccca | tgacaaagtc | cttgtgctcc | 720 |
| cgggcggcct | cgacgcaggc | ctgcgtgtac | tccttgttca | tgaagttgcc | ctggctggac | 780 |
| atttgggcga | ggatcaggag | gccgcggctc | agcggcgcct | cctcgatgcc | cgggaagagc | 840 |
| gactcgtcgc | cctcggcgat | ggcctttgtt | aaccggggcg | aggagacgga | ctcgtactgc | 900 |
| tgggtgacgg | tggtgatgga | gacgatgctg | cccttgcggc | cgtcgccgga | ccggttcgag | 960 |
| tagatgggct | tgtccaggac | gccaatggag | cccatgccgt | tgacgcgcc | ggcgggctcg | 1020 |
| gcgtccctgg | agtcggcgtc | gtcgtcaaac | gagtccatgg | tgggcgtgcc | gacggtgacg | 1080 |
| gacgtcttga | cctcgcaggg | gtagcgctcg | agccagcgct | tggcgccctg | ggccagcgag | 1140 |
| gccaccgacg | ccttgccggg | caccatgttg | acgttgacaa | tgtgcgccca | gtcgatgatg | 1200 |
| cgcgccgacc | cgcccgtgta | ctgcagctcg | acggtgtggc | caatgtcgcc | aaacttgcgg | 1260 |
| tcctcgaaga | tgaggaagcc | gtgcttgcgc | gccagcgacg | ccagctgggc | tcccgtgccc | 1320 |
| gtctccgggt | ggaagtccca | gcccgagacc | atgtcgtagt | gcgtcttgag | cacgacaatc | 1380 |
| gacgggccaa | tcttgtcggc | caggtacagc | agctcgcgcg | ctgtcggcac | gtcggcgctc | 1440 |
| aggcacaggt | tggacgcctt | gaggtccatg | agcttgaaca | ggtaagccgt | cagcgggtgc | 1500 |
| gtcgccgtct | cgctcctggc | cgcgaaggtg | gccttgagcg | tcgggtgtgg | tgccatggct | 1560 |
| gatgaggctg | agagaggctg | aggctgcggc | tggttggata | gtttaaccct | tagggtgccg | 1620 |
| ttgtggcggt | ttagagggg | ggaaaaaaaa | gagagagatg | gcacaattct | gctgtgcgaa | 1680 |
| tgacgttgga | agcgcgacag | ccgtgcggga | ggaagaggag | taggaactgt | cggcgattgg | 1740 |
| gagaatttcg | tgcgatccga | gtcgtctcga | ggcgagggag | ttgctttaat | gtcgggctcg | 1800 |
| tccctggtc | aaaattctag | ggagcagcgc | t | | | 1831 |

<210> SEQ ID NO 9
<211> LENGTH: 1507
<212> TYPE: DNA
<213> ORGANISM: Trichoderma reesei

<400> SEQUENCE: 9
atggcgccct cagttacact gccgttgacc acggccatcc tggccattgc ccggctcgtc    60

```
gccgcccagc aaccgggtac cagcacccccc gaggtccatc ccaagttgac aacctacaag    120
tgtacaaagt ccggggggtg cgtggcccag gacacctcgg tggtccttga ctggaactac    180
cgctggatgc acgacgcaaa ctacaactcg tgcaccgtca acggcggcgt caacaccacg    240
ctctgccctg acgaggcgac ctgtggcaag aactgcttca tcgagggcgt cgactacgcc    300
gcctcgggcg tcacgacctc gggcagcagc ctcaccatga accagtacat gcccagcagc    360
tctggcggct acagcagcgt ctctcctcgg ctgtatctcc tggactctga cggtgagtac    420
gtgatgctga agctcaacgg ccaggagctg agcttcgacg tcgacctctc tgctctgccg    480
tgtggagaga acggctcgct ctacctgtct cagatggacg agaacggggg cgccaaccag    540
tataacacgg ccggtgccaa ctacgggagc ggctactgcg atgctcagtg ccccgtccag    600
acatggagga acggcaccct caacactagc caccagggct tctgctgcaa cgagatggat    660
atcctggagg gcaactcgag ggcgaatgcc ttgacccctc actcttgcac ggccacggcc    720
tgcgactctg ccggttgcgg cttcaacccc tatggcagcg gctacaaaag gtgagcctga    780
tgccactact acccctttcc tggcgctctc gcggttttcc atgctgacat ggttttccag    840
ctactacggc cccggagata ccgttgacac ctccaagacc ttcaccatca tcacccagtt    900
caacacggac aacggctcgc cctcgggcaa ccttgtgagc atcacccgca agtaccagca    960
aaacggcgtc gacatcccca gcgcccagcc cggcggcgac accatctcgt cctgcccgtc    1020
cgcctcagcc tacggcggcc tcgccaccat gggcaaggcc ctgagcagcg gcatggtgct    1080
cgtgttcagc atttggaacg acaacagcca gtacatgaac tggctcgaca gcggcaacgc    1140
cggcccctgc agcagcaccg agggcaaccc atccaacatc ctggccaaca accccaacac    1200
gcacgtcgtc ttctccaaca tccgctgggg agacattggg tctactacga actcgactgc    1260
gcccccgccc ccgcctgcgt ccagcacgac gttttcgact acacggagga gctcgacgac    1320
ttcgagcagc ccgagctgca cgcagactca ctggggggcag tgcggtggca ttgggtacag    1380
cgggtgcaag acgtgcacgt cgggcactac gtgccagtat agcaacgact gttcgtatcc    1440
ccatgcctga cgggagtgat tttgagatgc taaccgctaa aatacagact actcgcaatg    1500
cctttag                                                              1507
```